US010653623B2

(12) United States Patent
Davagian et al.

(10) Patent No.: US 10,653,623 B2
(45) Date of Patent: May 19, 2020

(54) HYDROCORTISONE ACETATE SUPPOSITORY FORMULATION FOR TREATMENT OF DISEASE

(71) Applicant: Cristcot LLC, Concord, MA (US)

(72) Inventors: Jennifer J. Davagian, Concord, MA (US); Raj Devarajan, Acton, MA (US)

(73) Assignee: Cristcot LLC, Concord, MA (US)

( * ) Notice: Subject to any disclaimer, the term of this patent is extended or adjusted under 35 U.S.C. 154(b) by 0 days.

(21) Appl. No.: 15/555,325

(22) PCT Filed: Mar. 10, 2016

(86) PCT No.: PCT/US2016/021842
§ 371 (c)(1),
(2) Date: Sep. 1, 2017

(87) PCT Pub. No.: WO2016/145233
PCT Pub. Date: Sep. 15, 2016

(65) Prior Publication Data
US 2018/0036235 A1 Feb. 8, 2018

Related U.S. Application Data

(60) Provisional application No. 62/131,944, filed on Mar. 12, 2015.

(51) Int. Cl.
*A61K 9/02* (2006.01)
*A61K 47/02* (2006.01)
(Continued)

(52) U.S. Cl.
CPC ............ *A61K 9/025* (2013.01); *A61K 9/0031* (2013.01); *A61K 9/02* (2013.01); *A61K 31/573* (2013.01);
(Continued)

(58) Field of Classification Search
None
See application file for complete search history.

(56) References Cited

U.S. PATENT DOCUMENTS 6,136,337 A * 10/2000 Kondo ................. A61K 9/0031
424/436
7,635,709 B2 * 12/2009 Korsten ............... A61K 31/401
514/304

(Continued)

FOREIGN PATENT DOCUMENTS

| JP | 02178228 | * | 7/1990 |
| JP | H02 178228 A | | 7/1990 |
| WO | WO 2016/145233 A1 | | 9/2016 |

OTHER PUBLICATIONS

Rowe R.C. et al. (Colloidal Silicon Dioxide; Handbook of Pharmaceutical Excipients, p. 180-190; 2006). (Year: 2006).*

(Continued)

*Primary Examiner* — Robert A Wax
*Assistant Examiner* — Melissa S Mercier
(74) *Attorney, Agent, or Firm* — Hamilton, Brook, Smith & Reynolds, P.C.

(57) ABSTRACT

The present invention relates, in various embodiments, to formulations comprising hydrocortisone and silicon dioxide. In additional embodiments, the invention relates to suppositories comprising hydrocortisone and silicon dioxide. The formulations of the present invention are useful for administration to patients who have gastrointestinal diseases and disorders such as, for example, inflammatory bowel disease.

12 Claims, 11 Drawing Sheets

(51) Int. Cl.
    *A61K 31/573*    (2006.01)
    *A61K 9/00*      (2006.01)
    *A61K 47/10*     (2017.01)
    *A61K 47/14*     (2017.01)
    *A61K 47/20*     (2006.01)
    *A61M 31/00*     (2006.01)

(52) U.S. Cl.
    CPC .............. *A61K 47/02* (2013.01); *A61K 47/10* (2013.01); *A61K 47/14* (2013.01); *A61K 47/20* (2013.01); *A61M 31/007* (2013.01); *A61M 2210/1064* (2013.01); *A61M 2210/1067* (2013.01)

(56) References Cited

U.S. PATENT DOCUMENTS

2003/0185861 A1* 10/2003 Hori ................... A61K 9/0031
                                                     424/400
2010/0168563 A1   7/2010 Braver
2010/0322875 A1* 12/2010 Guilbaud ............... A61P 17/18
                                                     424/59

OTHER PUBLICATIONS

Baviskar et al. (Drug Delivery on Rectal Absorption: Suppositories, Int. J. Pharm. Sci.Rev.Res., 21(1), Jul.-Aug. 2013). (Year: 2013).*
International Search Report and Written Opinion of International Application No. PCT/US2016/021842, entitled: "Hydrocortisone Acetate Suppository Formulation for Treatment of Disease," dated May 24, 2016.
Rowe, R. C., et al., "Colloidal Silicon Dioxide," *Handbook of Pharmaceutical Excipients*, XP003016902; 180-190 (2006).
International Preliminary Report on Patentability of International Application No. PCT/US2016/021842, entitled: "Hydrocortisone Acetate Suppository Formulation for Treatment of Disease," dated Sep. 21, 2017.

* cited by examiner

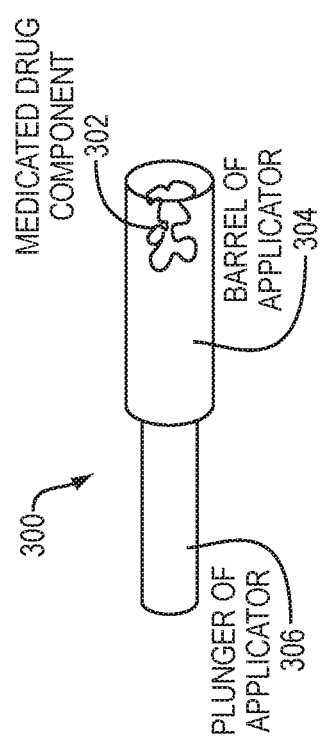

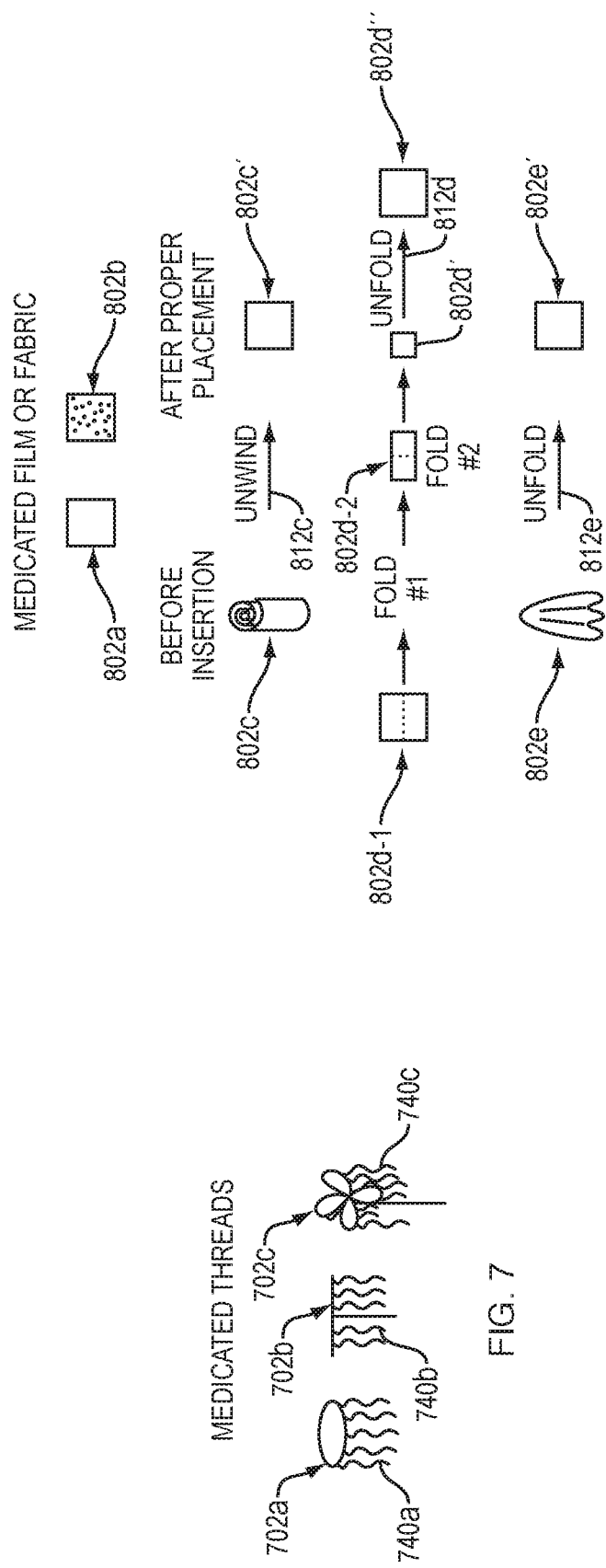

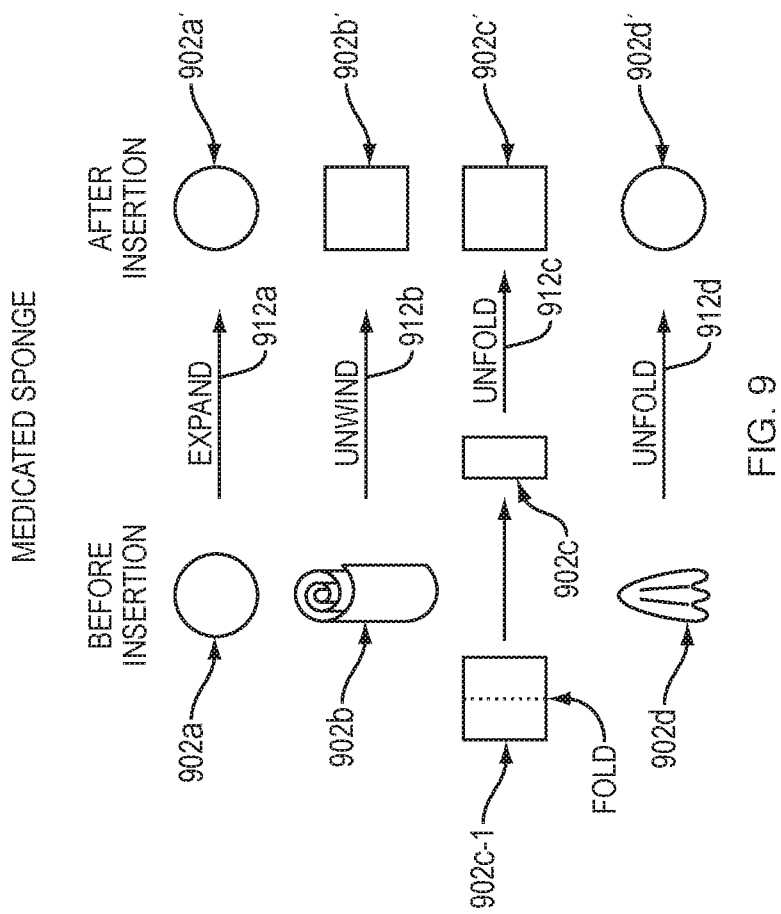

HYDROCORTISONE ACETATE SUPPOSITORY FORMULATION FOR TREATMENT OF DISEASE

This application is the U.S. National Stage of International Application No. PCT/US2016/021842, filed Mar. 10, 2016, which designates the U.S., published is English, and claims the benefit of U.S. Provisional Application No. 62/131,944, filed Mar. 12, 2015. The entire teachings of the above applications are incorporated herein by reference.

BACKGROUND OF THE INVENTION

Hydrocortisone delivered rectally has been established as a strong therapeutic treatment for certain medical conditions, including left-sided, distal ulcerative colitis. Advantages of rectally administered hydrocortisone (e.g., hydrocortisone acetate) include extremely low levels of systemic absorption and fewer side effects than are often experienced with oral and intravenous corticosteroid treatments. Current rectal drug formulations of hydrocortisone include liquid enemas, foam enemas and semi-solid suppositories. Current prescribing habits for rectal drug formulations of hydrocortisone include an assessment of the severity of the disease as well as the extent of disease activity within the colon.

Rectally-delivered hydrocortisone has been shown to induce remission in patients with left-sided, distal ulcerative colitis. For patients with this disease, liquid enemas are often prescribed because the medication is distributed as far as the splenic flexure. For patients with sigmoid colitis, foam enemas are prescribed as the distribution of the medication extends to the sigmoid colon and partially to the descending colon. Although ulcerative colitis confined to the rectum, defined as ulcerative proctitis, can be treated with suppository formulations of hydrocortisone, no suppository formulation of hydrocortisone has been approved by the Food and Drug Administration (FDA) as a safe and effective treatment.

Accordingly, there is a need for safer and more effective hydrocortisone suppository formulations for the treatment of gastrointestinal (GI) diseases and disorders, including ulcerative colitis, Crohn's disease and inflammatory bowel disease (IBD).

SUMMARY OF THE INVENTION

The present invention is based, in part, on the discovery of formulations of hydrocortisone having certain desirable properties and characteristics that render these formulations suitable for administration as a suppository to treat ulcerative colitis and other gastrointestinal diseases that are treatable with hydrocortisone.

Accordingly, in one embodiment, the present invention relates to a formulation comprising about 0.01% to about 25% by weight hydrocortisone acetate and about 0.001% to about 5% by weight colloidal silicon dioxide. In a particular embodiment, the formulation comprises about 0.5% to about 5% by weight hydrocortisone acetate and about 0.1% to about 5% by weight colloidal silicon dioxide. In a further embodiment, the formulation comprises about 4.5% by weight hydrocortisone acetate and about 0.7% by weight colloidal silicon dioxide. In some embodiments, the formulation additionally comprises an oleaginous base that includes triglycerides. In additional embodiments, the formulation also comprises butylated hydroxytoluene (BHT).

In other embodiments, the present invention relates to a suppository having a weight of about 2 grams (g), which comprises about 90 milligrams (mg) hydrocortisone acetate, and releases at least about 80% of the hydrocortisone acetate at about 180 minutes following exposure to dissolution media comprising a buffered 5% w/v sodium lauryl sulfate solution having a final pH in the range of about 6.8-7.0. In a particular embodiment, the suppository comprises about 90 mg hydrocortisone acetate, colloidal silicon dioxide, and an oleaginous base that includes triglycerides. In a particular embodiment, the suppository weighs about 2 g.

The formulations described herein have advantages over prior hydrocortisone suppository formulations, including, for example, improved retention by patients and reduced absorption variability. The disclosed formulations also have desirable release profiles of hydrocortisone acetate upon exposure to rectal fluid and, therefore, are less dependent than current hydrocortisone suppository formulations on melting temperature for the delivery of hydrocortisone to the patient.

In addition to the foregoing, embodiments of the invention are directed to the structure of the suppository. As known, certain diseases are treated by way of a suppository containing a drug (e.g., hydrocortisone acetate). Current suppositories have "torpedo" configurations and, therefore, can be difficult to apply in a rectum to effectuate a high level of drug delivery. Embodiments of the present invention provide for alternative configurations of suppositories that allow for easier application into the rectum and can provide greater surface area of the medication for which to expose tissues within the rectum.

Another embodiment of the invention is a drug delivery system (e.g., a suppository) that includes a component that changes shape or composition once inside the body and releases medication (e.g., hydrocortisone acetate) after being placed within the rectum. The component can be compact in shape and size for the administration into the body. Once the component is properly placed within the rectum, or at the anal-rectal line, the component changes shape or composition to administer the medication contained therein. The drug delivery component may be made of synthetic or biodegradable polymer impregnated with a medication. Alternatively, the component may be made of a metal with a polymer coating that is impregnated with the medication. The component may be composed of a water soluble base in combination with the drug. Alternatively, the component may encase or coat the drug in a water soluble film or coating.

One example embodiment includes a flexible ring that is made compact in shape and size before administration to the patient. The ring may be twisted or coiled to form a smaller ring within a ring. Alternatively, the ring may be folded to form a narrow loop, and, additionally, the ends of the narrow loop may be folded in on itself in the opposite direction, forming a compact shape of the ring. The ring may also be self-elongating in that it holds a small circumference before being placed within the body, at which time it expands in circumference to fit within the rectum.

Another embodiment includes a "tree" shape drug delivery component configured to fold into a compact formation until the proper placement within the body. The component may have one or more sections at the top of the tree that may fold down to a form "I" formation before administration. The component may or may not have a center stem. Alternatively, the sections at the top of the tree may be self-elongating in that they hold the "I" formation before administration and extend to the tree formation after proper placement within the body.

The embodiments of the ring or tree shapes may have medicated filaments that attach to the component. The medicated filaments may hang from the component within the body to treat a larger area of the mucosa lining of the rectum. The filaments may degrade within the body or be expelled from the body after releasing the medication.

An alternative drug delivery system includes a fabric impregnated with medication or a film composed of the medication. The fabric may be folded or wound on itself before administration. After proper placement, the fabric may be unfolded or unwound to adhere to the lining of the rectum.

Another example embodiment includes a sponge impregnated with medication that is folded, compressed or wound on itself before administration to hold a more compact shape. After administration, the sponge may expand, unfold, or unwind to fit the shape and location within the rectum.

Another drug component includes a container that holds the medication in a compact shape or form until it is properly placed within the body. One example embodiment includes a water-soluble shell surrounding a drug composition. Once the drug component is properly placed within the rectum, the outer shell dissolves. The medication within the shell expands or changes shape or form and releases the drug to be absorbed by the body. The medication, in a solid state, may be formed in a variety of structural shapes as disclosed herein. When packaged within a delivery vessel, such as an inactive ingredient that is designed to change state over time after placement within the body to release medication contained therein, the medication may include, but is not limited to, the following forms: powder, liquid, gel, granule, or threads. The medication may increase its contact with the mucosa lining of the rectum by expanding in volume. Alternatively, the medication may increase its contact with the mucosa lining of the rectum by greater disbursement of the drug after being freed from the constraints of the outer shell.

Another embodiment includes a water soluble shell surrounding a solid or semi-solid drug that expands or takes a different shape after the drug component is properly placed within the body.

The drug components described in this application can be administered to the patient using an insertion applicator to achieve proper placement within the body.

BRIEF DESCRIPTION OF THE DRAWINGS

FIG. 3 is a diagram of a medicated drug component according to an embodiment of the present invention within a device configured to insert the component into a rectum.

FIGS. 7-9 are diagrams of other embodiments of the medicated drug component.

DETAILED DESCRIPTION OF THE INVENTION

Figure 1:
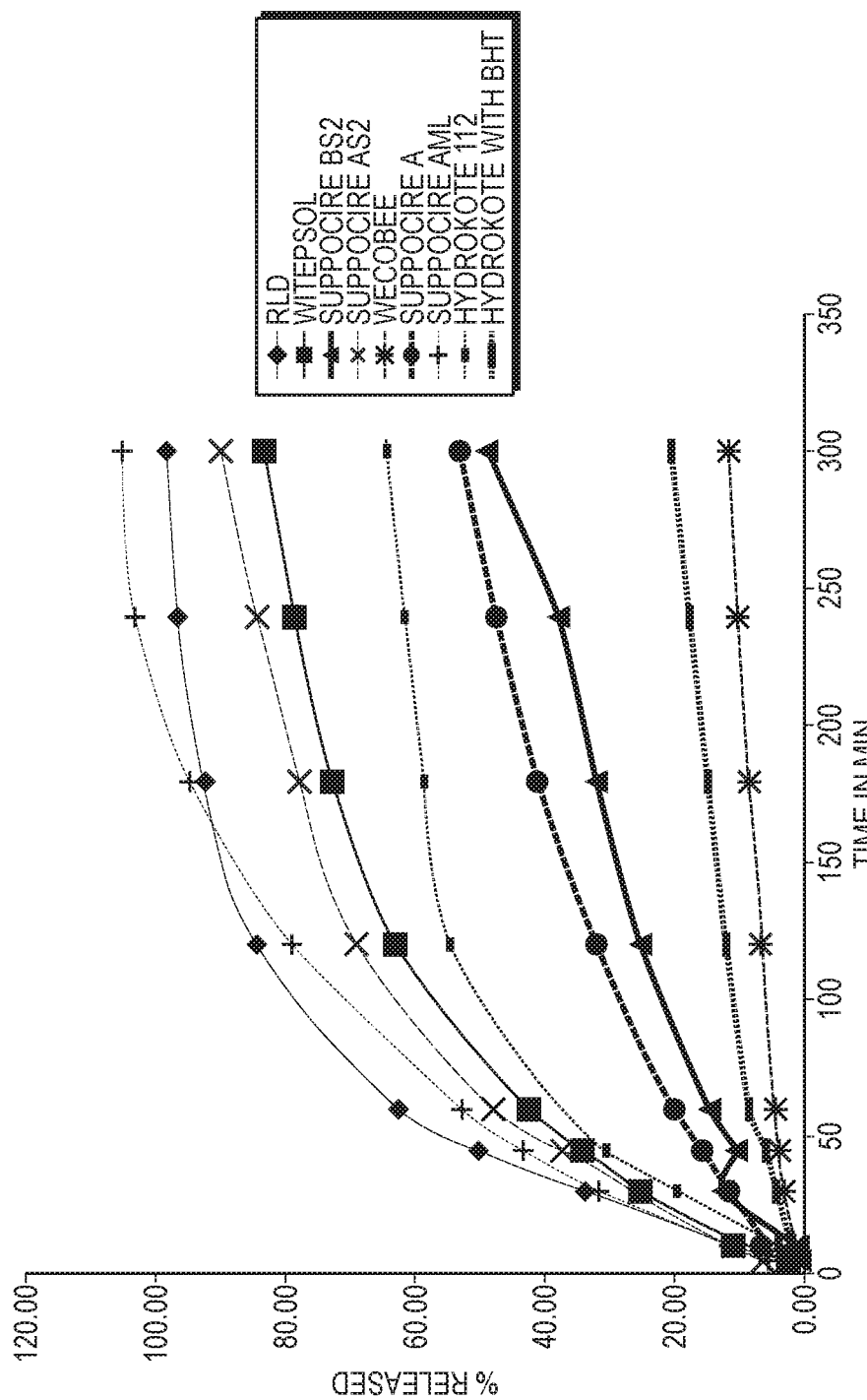
FIG. 1 is a graph showing a dissolution profile for eight prototype hydrocortisone formulations in media that mimics rectal fluid.

A description of example embodiments of the invention follows.

In one embodiment, the invention relates to a formulation comprising hydrocortisone (e.g., hydrocortisone acetate) and silicon dioxide (e.g., colloidal silicon dioxide). In some embodiments, the formulation comprises about 0.01% to about 25% by weight hydrocortisone acetate. For example, the formulation can comprise about 0.02% to about 1.0%, about 0.03% to about 0.1%, about 0.4% to about 10.0%, about 3.0% to about 8.0%, about 4.0% to about 7.0%, or about 4.0% to about 5.0% by weight hydrocortisone acetate. In another embodiment, the formulation comprises about 0.5% to about 5% by weight hydrocortisone acetate. In a particular embodiment, the formulation comprises about 4.5% (e.g., 4.0%, 4.5%, 5.0%) by weight hydrocortisone acetate.

In some embodiments, the formulation comprises about 0.001% to about 5% by weight colloidal silicon dioxide. For example, the formulation can comprise about 0.002% to about 1%, about 0.003% to about 0.1%, about 0.004% to about 0.05%, about 0.4% to about 1.5%, or about 0.5% to about 1.0% by weight colloidal silicon dioxide. In another embodiment, the formulation comprises about 0.1% to about 5% by weight colloidal silicon dioxide. In a particular embodiment, the formulation comprises about 0.7% (e.g., 0.6%, 0.7%, 0.8%) by weight colloidal silicon dioxide.

In additional embodiments, the formulation further comprises a pharmaceutically-acceptable excipient (e.g., a pharmaceutically-acceptable excipient other than colloidal silicon dioxide). In some embodiments, the formulation comprises a pharmaceutically-acceptable excipient that is an oleaginous base. The oleaginous base can be naturally occurring, semi-synthetic or synthetic. In certain embodiments, the oleaginous base includes glycerides (e.g., monoglycerides, diglycerides and triglycerides). For example, the oleaginous base can include a mixture of monoglycerides, diglycerides and triglycerides, in a variety of ratios. In a particular embodiment, the oleaginous base includes triglycerides (e.g., more than 50% of the glyceride content is triglycerides).

Suitable oleaginous bases for use in the formulations described herein include, for example, theobroma oil/cocoa butter, triglycerides from vegetable oils, hydrogenated cocoglycerides, trilaurin triglycerides (glycerol trilaurate, glyceryl trilaurate, glyceryl tridodecanoate, glycerin trilaurate and tridodecanoin), lecithin and hydrogenated lecithin, synthetic or semi-synthetic triglycerides and mixtures thereof. In some embodiments, the formulation includes triglycerides from a hydrogenated vegetable oil. The vegetable oil can be, e.g., a palm oil, a palm kernel oil, a cottonseed oil, a soybean oil, a rapeseed oil, a coconut oil, a peanut oil, a sunflower seed oil or an olive oil. In other embodiments, the oleaginous base is a semi-synthetic glyceride base comprising saturated C8-C18 triglyceride fatty acids and lecithin. In a particular embodiment, the oleaginous base comprises at least about 85% triglycerides, and further comprises diglycerides and monoglycerides (e.g., less than about 15% diglycerides and less than about 1% monoglycerides). Examples of commercially available oleaginous bases that are useful for the formulations described herein include, for example, WECOBEE® M bases, HYDRO-KOTE® C and 112 bases, WITEPSOL® H-15 bases, and SUPPOCIRE® A, AS2, AML, and BS2 bases.

In other embodiments, the formulation comprises a pharmaceutically-acceptable excipient that is a water-soluble miscible base. Examples of water-soluble miscible bases include glycerinated gelatins or polyethylene glycol (PEG) polymers (e.g., PEG 300, PEG 1450, PEG 3350, PEG 6000, PEG 8000).

In certain embodiments, the formulation further comprises an additive (e.g., one additive, two or more additives). Additives include, but are not limited to, adsorbents, surface acting agents (e.g., mucosal adhesives, such as xanthan gum, lisinopril, hydroxypropyl methylcellulose, carboxy methylcellulose, and chitosan, among others), viscosity-influencing agents, suspending/dispersing agents (e.g., zinc oxide, alginic acid, crystalline cellulose), plasticizers (e.g., diethylhexyl phthatale, glycerin), melting point-adjusting agents (e.g., white wax), antimicrobial agents (e.g., thimerasol), phospholipides (e.g., lecithin) and antioxidants (e.g., ascorbic acid, ascorbic palmitate, butylated hydroxytoluene (BHT), butylated hydroxyanisole (BHA)).

In some embodiments, the formulation comprises an additive that is an antioxidant. Particular examples of antioxidants that are suitable for inclusion in the formulations described herein include butylated hydroxytoluene (BHT) and butylated hydroxyanisole (BHA), as well as combinations BHT and BHA, in a variety of ratios (e.g., a 1:1 ratio). In a particular embodiment, the formulation comprises butylated hydroxytoluene (BHT). For example, the formulation can comprise about 0.001% to about 0.1%, about 0.005% to about 0.03%, or about 0.0095% to about 0.015% by weight BHT. In a particular embodiment, formulation comprises about 0.01% (e.g., 0.0095%, 0.010%, 0.015%) by weight BHT.

In general, the formulations described herein are solid or semi-solid formulations. Accordingly, in various embodiments, the formulations of the present invention are suitable for use in a suppository for administration (e.g., rectal administration) to a mammal (e.g., a human). Typically, the formulations described herein have one or more properties (e.g., melting temperature, solubility, stability) that are desirable for suppositories. For example, in some embodiments, the formulation releases the hydrocortisone acetate upon exposure to rectal fluid. Methods for assessing whether a formulation releases the hydrocortisone acetate upon exposure to rectal fluid are known in the art and include, for example, the method exemplified herein.

In additional embodiments, the formulation has a melting temperature in the range of about 35° C. to about 41° C., preferably about 36° C. to about 40° C., more preferably about 37° C. to about 39° C. Methods for determining the melting temperature of a formulation are known in the art and include, for example, the method exemplified herein.

In some embodiments, the formulation is stable (e.g., under storage conditions) at a temperature in the range of about 25° C. to about 40° C. Methods for assessing whether a formulation is stable under storage conditions are known in the art and include, for example, the method exemplified herein.

In other embodiments, the invention relates to a suppository having a weight of about 2 grams (g), which comprises about 90 milligrams (mg) hydrocortisone acetate, and releases at least about 80% of the hydrocortisone acetate at about 180 minutes following exposure to dissolution media comprising a buffered 5% w/v sodium lauryl sulfate solution having a final pH in the range of about 6.8-7.0. In a particular embodiment, the dissolution media comprises 5% w/v sodium lauryl sulfate:acetate buffer pH 5.0 (70:30) final pH adjusted to 6.8-7.0.

Suitable concentrations of hydrocortisone acetate for use in the suppositories described herein include, for example, any of the concentrations of hydrocortisone acetate described herein as being suitable for the formulations of the invention. Suitable concentrations of colloidal silicon dioxide for use in the suppositories described herein include, for example, any of the concentrations of colloidal silicon dioxide described herein as being suitable for the formulations of the invention. In one embodiment, the suppository comprises 90 mg of hydrocortisone (e.g., hydrocortisone acetate) and about 5 mg to about 20 mg (e.g., about 14 mg) of colloidal silicon dioxide.

In some embodiments, the suppository further comprises an oleaginous base. In one embodiment, the oleaginous base includes triglycerides. Suitable oleaginous bases for use in the suppositories described herein include, for example, a semi-synthetic glyceride base comprising saturated C8-C18 triglyceride fatty acids and lecithin, or comprising at least about 85% triglycerides, wherein the base further comprises diglycerides and monoglycerides.

In additional embodiments, the suppository further comprises an additive. Suitable additives for use in the suppositories described herein include, for example, any of the additives described hereinabove as being suitable for the formulations of the invention. In a particular embodiment, the suppository comprises BHT. Suitable concentrations of BHT for use in the suppositories described herein include, for example, any of the concentrations of BHT described hereinabove as being suitable for the formulations of the invention.

The suppositories described herein can have a weight in the range of about 500 mg to about 5 g and generally include from about 5 mg to about 200 mg of hydrocortisone (e.g., hydrocortisone acetate). In a particular embodiment, the suppository weighs about 2 g (e.g., 1.8 g, 1.9 g, 2.0 g, 2.1 g, 2.2 g). In one embodiment, the suppository weighs about 2 g and comprises about 90 mg (e.g., 85 mg, 90 mg, 95 mg) hydrocortisone acetate. In a further embodiment, the suppository weighs about 2 g and comprises about 90 mg hydrocortisone acetate and about 14 mg (e.g., 12 mg, 13 mg, 14 mg, 15 mg, 16 mg) colloidal silicon dioxide. In a further embodiment, a suppository weighs about 2 g and comprises about 90 mg hydrocortisone acetate, about 14 mg colloidal silicon dioxide and about 0.2 mg (e.g., 0.15 mg, 0.20 mg, 0.25 mg) BHT.

In some embodiments, the suppository has a weight of about 2 g, comprises about 90 mg of hydrocortisone acetate, and releases at least about 80% of the hydrocortisone acetate at about 180 minutes following exposure to a dissolution media comprising 5% w/v sodium lauryl sulfate:acetate buffer pH 5.0 (70:30) final pH adjusted to 6.8-7.0.

In some embodiments, the present invention relates to a suppository having an oblong shape. In other embodiments, the oblong shape further comprises a cylindrical shape. In certain embodiments, the suppository has a shape that allows contact between the outer surface of the suppository and the mucosal membrane of the rectum when the suppository is situated in the rectum. In other embodiments, the suppository formulation releases the hydrocortisone acetate upon exposure to rectal fluid.

Methods and devices for administering suppositories are known in the art and include, for example, those described in U.S. Pat. No. 8,192,393 B2, the contents of which are incorporated herein by reference in their entirety. Such methods and devices are useful for administration of the formulations (e.g., suppositories) described herein.

The formulations (e.g., suppositories) described herein are useful for the treatment of gastrointestinal diseases and disorders, including, for example, inflammatory bowel disease (IBD), bowel ailments and other diseases for which systemic or local rectal hydrocortisone is an appropriate therapeutic intervention. Such gastrointestinal diseases and disorders include, but are not limited to, colitis (e.g., ulcerative colitis, collagenous colitis, lymphocytic colitis), Crohn's disease, proctitis (e.g., ulcerative proctitis), and hemorrhoids (e.g., internal hemorrhoids).

In some embodiments, the formulations (e.g., suppositories) described herein can be administered in combination with other therapeutic agents that are useful for treating gastrointestinal diseases and disorders. In one embodiment, the formulations (e.g., suppositories) described herein can be administered in combination with mesalamine (e.g., oral mesalamine, a suppository containing mesalamine). In general, the other agent(s) being administered in combination with the hydrocortisone formulations will be administered separately from the hydrocortisone formulation (e.g., in a different form (e.g., a pill or capsule) or suppository). In some embodiments, the formulations (e.g., suppositories) described herein can be administered in combination with a local anesthetic (e.g., lidocaine).

Ailments and diseases of the bowel are common and have varying degrees of severity. One of the difficulties of treating patients with bowel disorders and symptoms is targeting the affected area. Oral medications must pass through the metabolism before offering therapeutic benefit and are systemic in their reach. Increasingly, the intravenous infusion therapies are being used to treat bowel disease and are targeted to modify the immune system.

One subset of patients with digestive disease suffer from ulcerative proctitis which affects the rectum and cannot be treated with oral or intravenous medications. Treatment for ulcerative proctitis is best accomplished with local therapy using medications that can treat the venous inflammation topically. Current drug therapy for ulcerative proctitis includes the use of suspension enemas, suppositories and creams or ointments. In the case of internal ulcers, the target area is the anal-rectal line and the lower rectum where inflamed veins originate and are sometimes prolapsed.

Suspension enemas are designed to treat the sigmoid or left side of the colon and place the drug too far above the lower rectum and the affected area. Enema medication is also difficult to retain, and often patients must be sedated in order to complete the therapy. Suppositories administered with a finger are placed too shallow within the anal canal and do not reach the lower rectum and anal-rectal line. Additionally, the suppository medication is difficult to retain and often leaks from inside to outside the body. Creams and ointments are primarily used to treat external sores and, when used internally, do not reach the targeted area for ulcers due to ulcerative proctitis inside the rectum at or above the anal-rectal line.

A drug component that places medication in the targeted location of the lower rectum is the optimal way to treat ulcerative proctitis. When placed in the targeted location, not only does the drug avoid contact with the sphincter muscles that signal the brain to release the contents of the colon, but also the drug is placed at the origins of hemorrhoid inflammation.

Targeted topical therapy would be a benefit in the treatment of inflammatory bowel disease, in particular, ulcerative proctitis. Affecting the lower six inches of the colon, ulcerative proctitis is best treated with topical therapy. However, in order to prevent the advancement of the disease, the area of treatment should be at the highest point of the inflammation. Treatment of ulcerative proctitis patients has similar drawbacks to the treatment of resulting ulcers with suspension enemas and suppositories.

FIG. 3 illustrates the use of an insertion applicator 300 for the administration of a drug component into the body of the patient in its pre-insertion shape or form. An example of an insertion applicator is described in U.S. application Ser. No. 12/287,215, entitled "Method And Apparatus For Inserting A Rectal Suppository," filed on Oct. 7, 2008, now U.S. Pat. No. 8,192,393, the entire teachings of which are incorporated herein by reference. In an example embodiment, the drug component 302 is placed in a distal end 308 of an insertion barrel 304 in its pre-insertion form or shape. In a different example embodiment, the drug component 302 is placed in a proximal end 310 of the barrel 304. A plunger 306 is thereafter placed in the proximal end of the barrel 304. After inserting the applicator 300, filled with the drug component, into the anus, the plunger 306 is advanced from the proximal end to the distal end of the barrel, thereby releasing the drug component 302 to the proper positioning within the rectum (see also FIGS. 5A-5B). Once the drug component 302 is properly positioned within the body, the drug component changes shape or form and releases its therapeutic medication to the mucosa lining of the rectum (see also FIG. 5C).

Figure 4A:
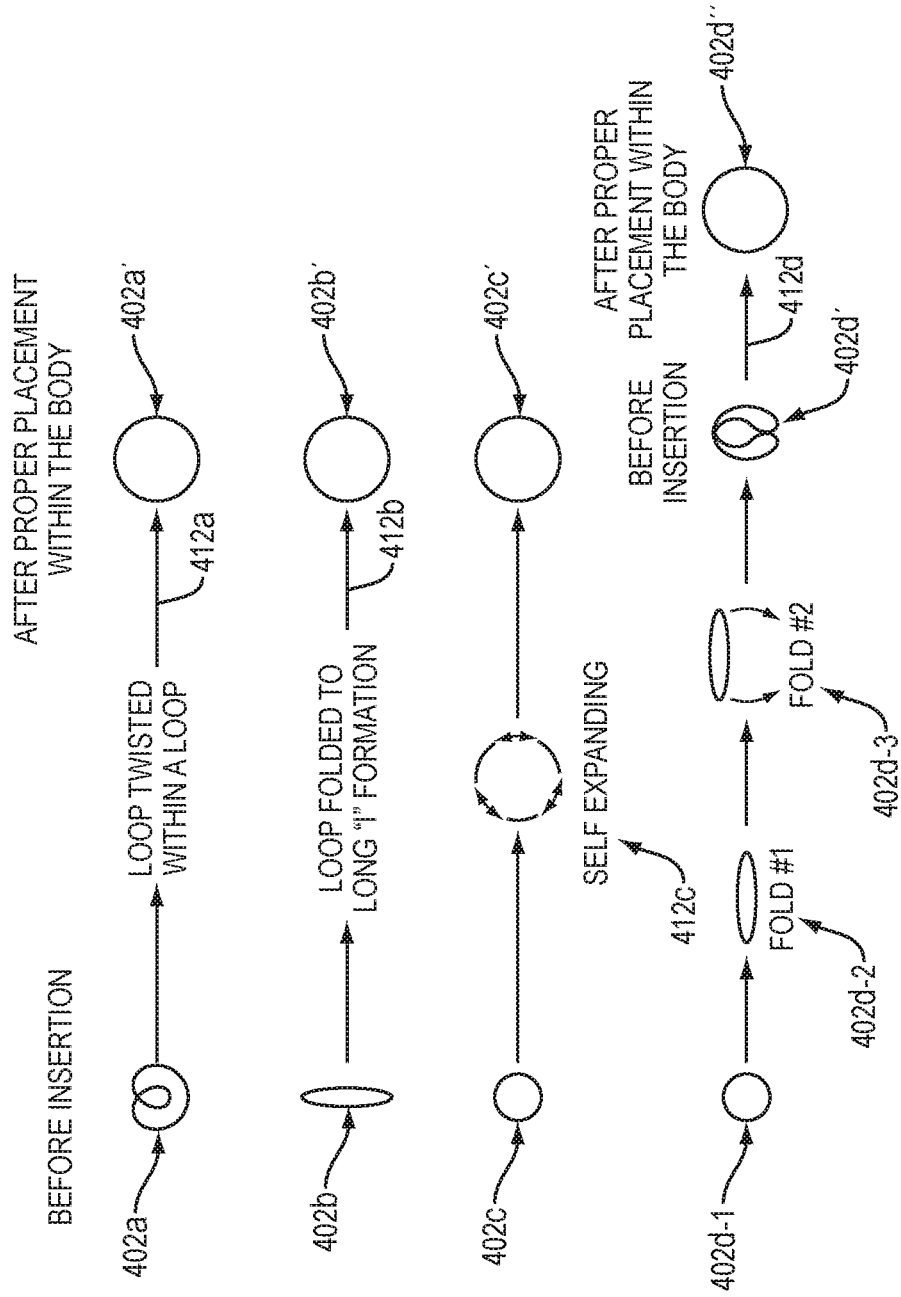
FIGS. 4A and 4B are diagrams of ring or other shaped embodiments of medicated drug components.

FIG. 4A illustrates example embodiments of folded (collapsed) medicated rings 402a, 402b, 402c, and 402d' (collectively 402) in their pre-insertion shape and their new shape after proper positioning within the body. After deployment, the medicated ring 402 unfolds, uncoils, or expands (412a, 412b, 412c, 412d) depending on the way it was compressed to the smaller shape. The medicated ring 402 unfolds or expands to a size whereby it is thereafter configured to press on tissue of the rectum (see also FIG. 5C). The unfolded or expanded state of ring 402 is indicated for the example embodiments in FIG. 4A at 402a', 402b', 402c' and 402d''. Once in position, the medicated ring 402 releases the medication contained within the component. The component thereafter either degrades within the body or is released during the evacuation of the contents of the colon.

As illustrated in FIG. 4A, a flexible ring 402 is made compact in shape and size before administration to the patient. For example, ring 402a may be twisted or coiled to form a smaller ring (loop) within a ring (loop). The ring 402a untwists or uncoils (412a) after proper placement within the body. In another example, ring 402b may be folded to a loop in a long "I" formation before placement and is configured to unfold (412b) after placement within the body. A ring 402c may also be self-elongating (e.g., self-expanding, as shown at 412c) in that it holds a small circumference before and until being placed within the body, at which time it expands in circumference to fit within the rectum. Alternatively, ring 402d-1 may be folded to form a narrow loop 402d-2, and, additionally, opposite ends of the narrow loop may be folded in on themselves (402d-3), forming a compact shape of the ring 402d' before insertion. The ring 402d' then unfolds (412d) to an expanded shape 402d'', after proper placement.

Figure 4B:
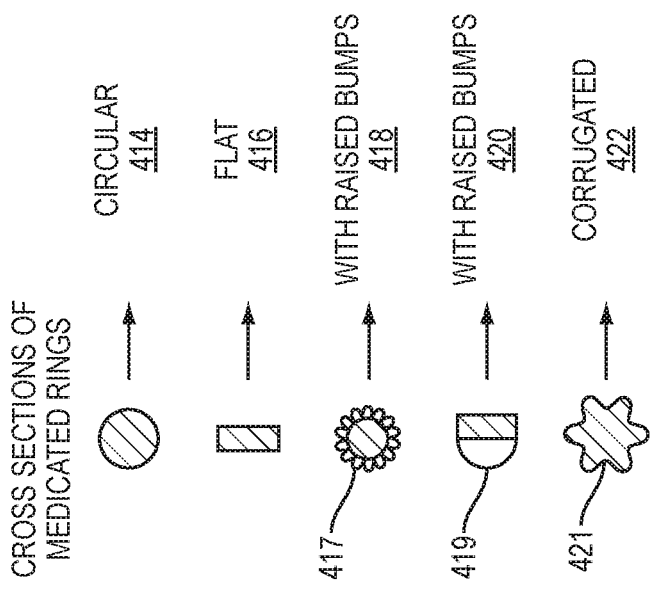

FIG. 4B illustrates cross sections of drug components, such as rings 402 of FIG. 4A, that may be circular 414 in cross section or straight (e.g., flat) 416 in cross section. An outer side of the drug components may have one or more raised bumps to aid in the adherence to the mucosa lining of the rectum. For example, component 418 is circular in cross section and includes raised bumps 417 arranged around its perimeter. In another example, component 420 is flat in cross section and includes raised bumps 419 on at least one side. Alternatively, the drug components may be corrugated 422 with alternating grooves 421 that aid in the positioning within the rectum.

Figure 5A:
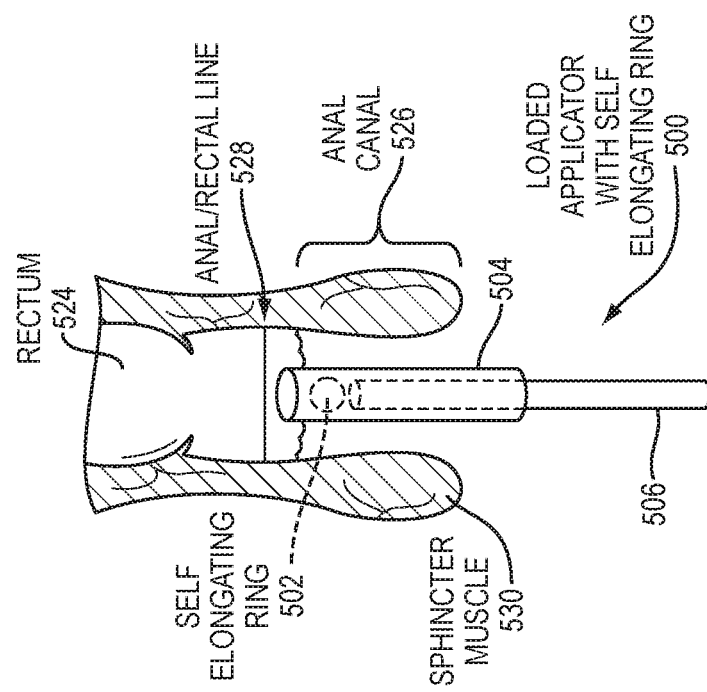
FIGS. 5A-5C are diagrams illustrating a sequence by which a suppository insertion device according to an embodiment of the present invention is used to insert a suppository (e.g., a medicated drug component) into a rectum.
Figure 5C:
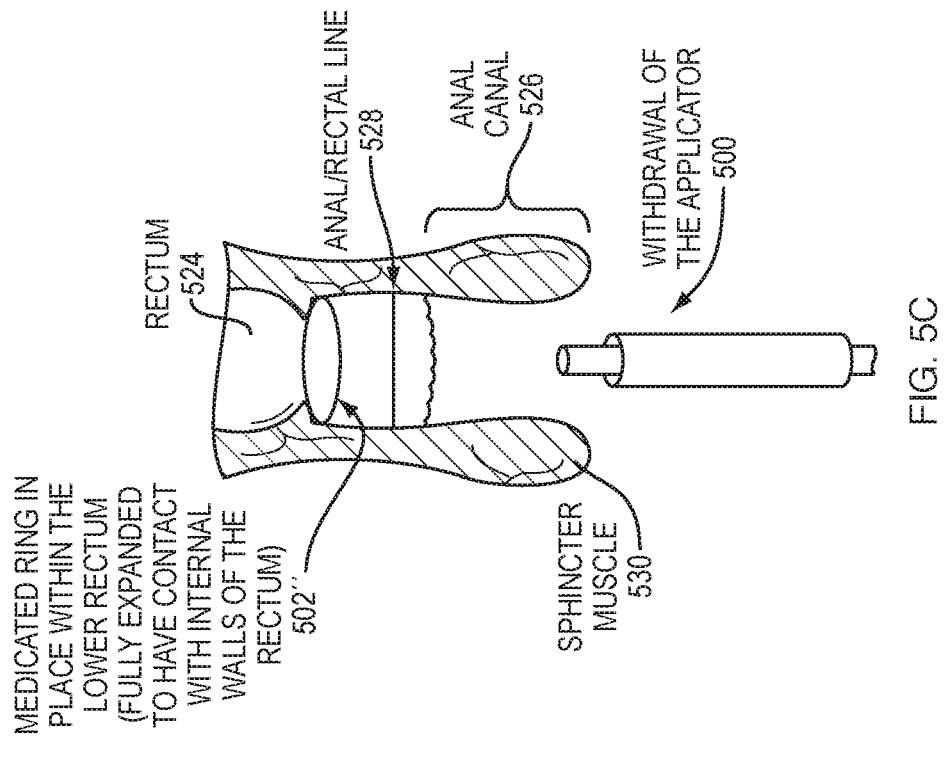
Figure 5B:
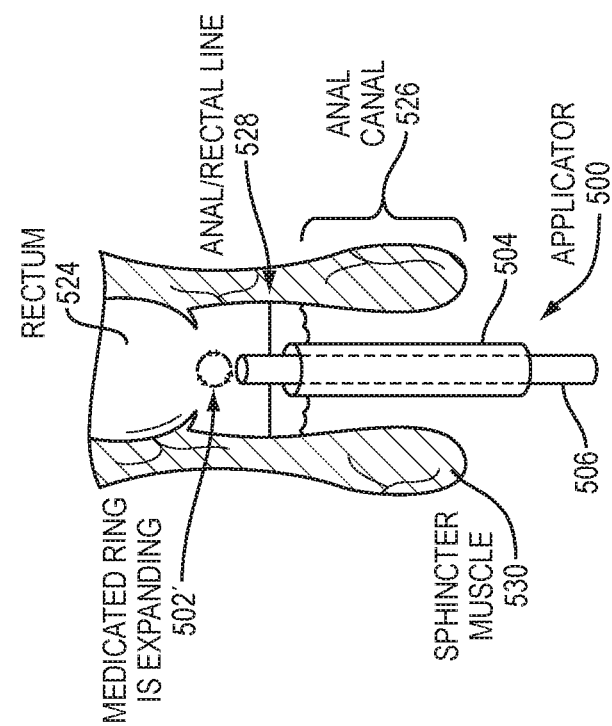

FIGS. 5A-5C illustrate a process by which a person inserts a suppository (e.g., a medicate drug component) 502 into a rectum 524 through use of a suppository insertion device 500 according to an embodiment of the present invention. In FIG. 5A, a barrel 504 of the insertion device 500 is inserted into an anal canal 526 below the anal-rectal line 528. A suppository 502 and plunger 506 may be inside the barrel 504 during the insertion of the barrel. In FIG. 5B, the person pushes the plunger 506 toward the anal-rectal line 528, which, in turn, pushes the suppository 502 toward and into the rectum 524, at or above the anal-rectal line and past the sphincter muscles 530. Once released from the insertion device 500, the suppository 502 can change shape or form, e.g., expand, as illustrated at 502'. FIG. 5C illustrates the suppository in an expanded form 502" in which the suppository's expanded size causes it to have contact with internal walls of the rectum 524. The applicator 500 is withdrawn, leaving the suppository in place. The suppository 502" is thereafter removed from the rectum through normal discharge of contents from the bowel in accordance with various embodiments of the suppository, as described herein.

Figure 6B:
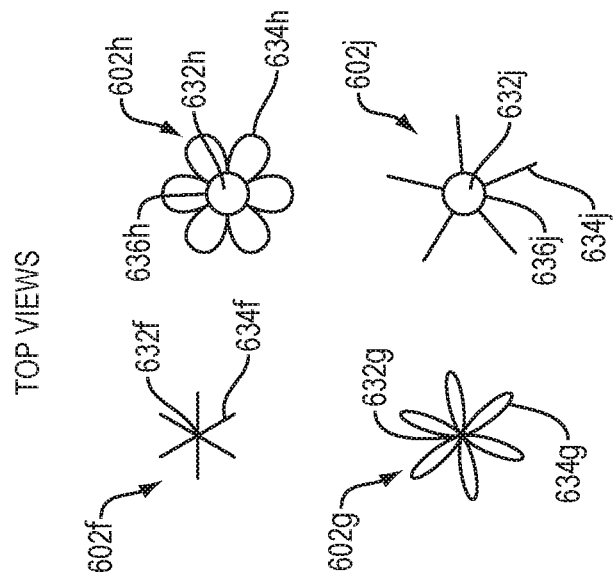
FIGS. 6A and 6B are diagrams of tree-shaped embodiments of the medicated drug component.
Figure 6A:
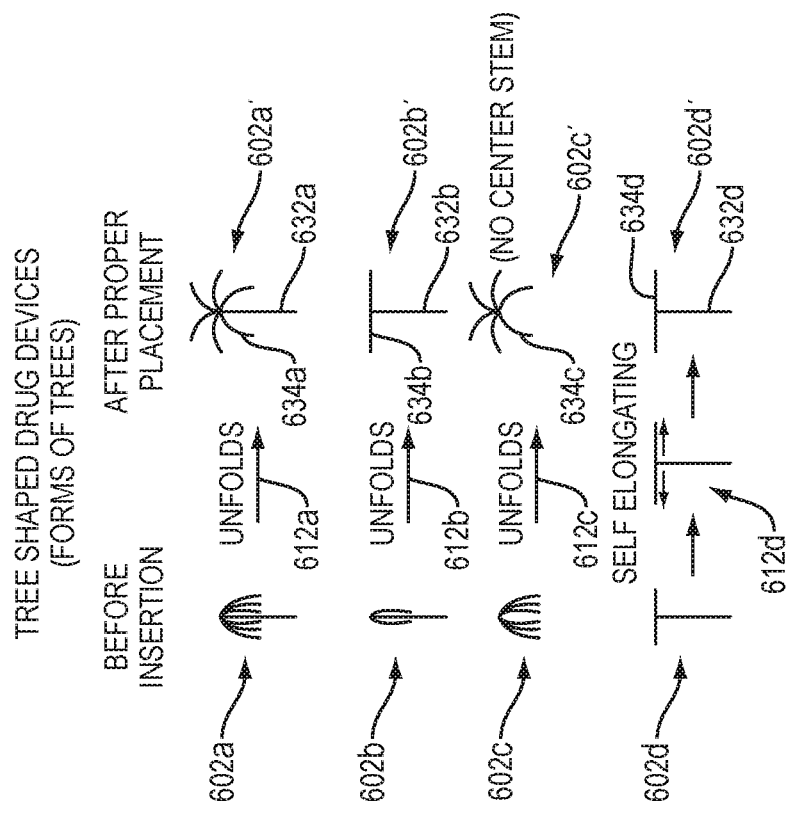
Figure 6C:
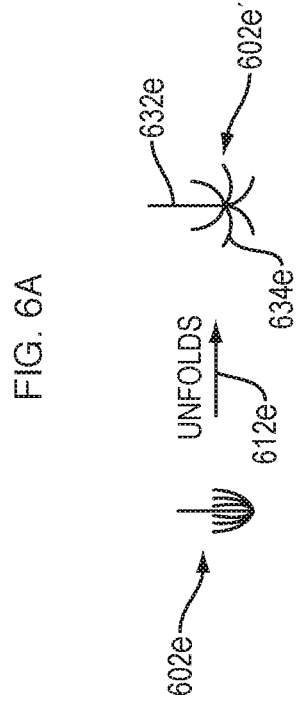
FIG. 6C is another embodiment of the drug component.

FIGS. 6A and 6C illustrate example embodiments of folded medicated tree components 602a, 602b, 602c, 602d, and 602e (collectively, 602) in their pre-insertion shape and their new shape 602a', 602b', 602c', 602d' and 602e' after proper positioning within the body. The medicated tree 602 unfolds or self expands (612a, 612b, 612c, 612d, 612e), depending on the way it was compressed to the smaller shape. The medicated tree 602 unfolds or expands to a size whereby it will be configured to press on the tissue of the rectum. The tree 602 may have a center stem (632a, 632b, 632d, 632e) or a center ring (see, e.g., 636h and 636i in FIG. 6B) from which the arms (634a, 634b, 634d, 634e) of the tree radiate. Alternatively, a tree 602c can have arms 634c radiating from a central point and not have a center stem. Once in position, the medicated tree releases the medication contained within the drug component. The drug component either degrades within the body or is released during the evacuation of the contents of the colon.

The "tree trunk" may be made of the same material as the "branches" of the tree and degrade in the body. Alternatively, the tree trunk may be made of a soft cushiony material that causes no harm and holds a shape that can be expelled with the contents of the bowel.

FIG. 6B illustrates top views of tree-shaped drug components. The tree-shaped drug components (602f, 602g, 602h and 602j) may have one or more arms (634f, 634g, 634h and 634j) radiating out from a center position (632f, 632g, 632h, 632j). The arms may be in a straight stick (634f, 634j) or a petal formation (634g, 634h). The arms may meet at the center point (632f, 632g) or they may radiate from a ring (636h, 636j) surrounding the center point (632h, 632j), thereby allowing gas to flow through the center of the drug component.

FIG. 6C illustrates a tree drug component 602e unfolding (612e) upside down, with the center post 632e and the free ends of the tree branches 634e entering the body first.

FIG. 7 illustrates medicated filaments (e.g., mediated threads) attached to the drug component. Three example configurations are shown. One or more medicated filaments 740a, 740b, and 740c can be attached, or otherwise coupled, to a ring-shaped drug component 702a, tree-shaped drug component 702b (having a center portion and arms), and flower-shaped drug component 702c (having a center stem and petals). A drug (e.g., an active ingredient) can be carried by or embedded into the filaments. The medicated filaments 740a, 740b, 740c may hang from the component within the body to treat a larger area of the mucosa lining of the rectum. The filaments may degrade within the body or be expelled from the body after releasing the medication.

FIG. 8 illustrates a medicated film 802a and a medicated fabric 802b. The drug and a water soluble binding agent may compose the film 802a. The fabric 802b may be impregnated with the drug or have raised bumps on the fabric that contain the drug. Both embodiments can be rolled (802c), folded (802d) or draped (802e) before insertion, and can unwind (812c) or unfold (812d, 812e) to a new shape (802c', 802d" and 802e') after proper placement within the body. The film or fabric may be folded multiple times, e.g., along one axis (802d-1) and then along another, e.g., perpendicular, axis 802d-2. The fabric or film may adhere to the lining of the rectum and deliver the medication to the area within which it comes in contact. The medicated film or fabric provides localized therapy to an affected area, which can be of benefit when treating specific areas of the colon, for example, the anal-rectal line, where the swelling of hemorrhoid veins originate.

FIG. 9 illustrates medicated sponges 902a, 902b, 902c and 902d (collectively, 902) that can be compressed (902a), wound on itself (902b), or folded (902c, 902d) to take a smaller pre-insertion shape and size. Folding can include folding the sponge once (902c-1), as illustrated, or multiple times, e.g., along different axes. After proper positioning within the body, the sponges 902 may expand (912a), unwind (912b), or unfold (912c, 912d) to a new shape (902a', 902b', 902c' and 902d') and release the medication within.

Figure 10A:
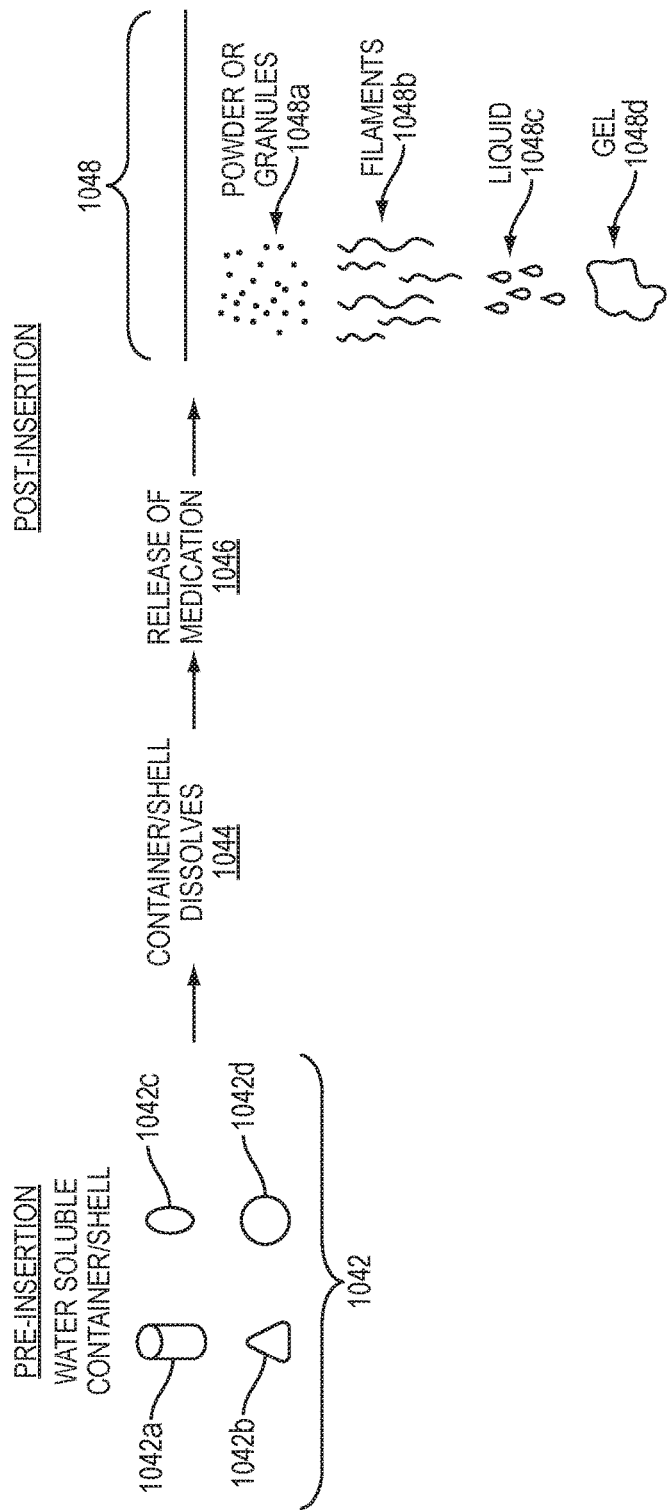
FIGS. 10A and 10B are flow diagrams indicating example application techniques for the mediated drug component.

FIG. 10A illustrates various embodiments of water soluble shells 1042a, 1042b, 1042c, and 1042d (collectively, 1042) that contain medication. The shells can have any suitable shape, such as spherical, cylindrical, rectangular and triangular and the like. The medication includes an active drug ingredient and can be contained in the shell in a stable form. The shells 1042 are configured to dissolve (1044) and release (1046) the medication. The medication, which may be contained in the shell 1042 in any suitable form, can be released in a new form 1048, such as powder or granules 1048a, embedded or attached to filaments 1048b, a liquid 1048c, or a gel 1048d. The new form can differ from the stable form.

Figure 10B:
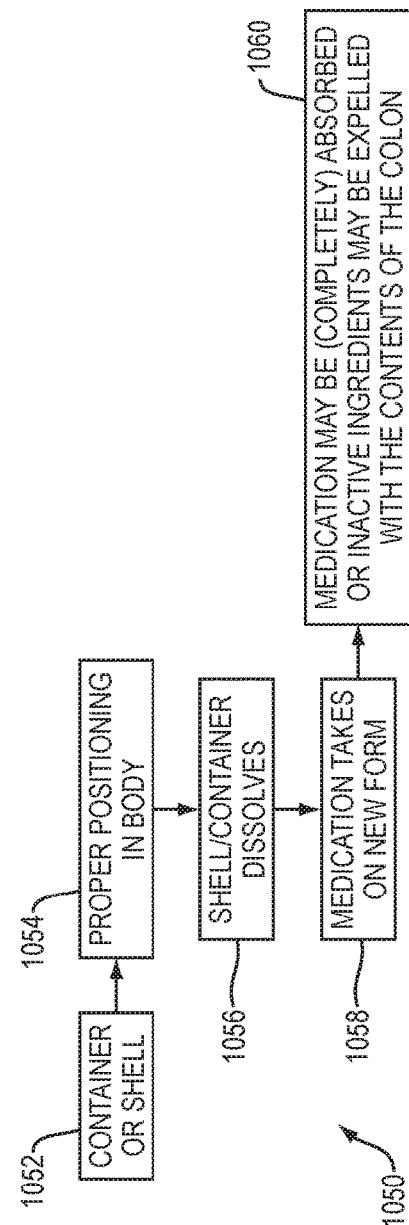

FIG. 10B is a flow diagram 1050 illustrating an example of the change in a form that the drug component makes after proper positioning in the body. The drug component may be administered to the patient using an insertion applicator. At 1052, a drug component is provided that includes medication contained in a shell or other suitable container. At 1054, the drug component is administered to achieve proper positioning in the body. Once properly positioned in the body, the shell dissolves (1056), thereby allowing the medication to be released in a new form (1058), including, but not limited to, powder or granules, filaments, liquid or gel (see also FIG. 10A). At 1060, the medication may be completely absorbed by the body. Alternatively or in addition, inactive ingredients in the formulation may be expelled with the contents of the colon. There may be more than one change in form. After a first dissolution of an outer shell and release of a medication, there may be a second shell to dissolve and, thus, release another treatment of medication in the same or different form from the first release.

As used herein, the term "about" when used in the context of the weight of a suppository, or the amount or percent by weight of a particular ingredient in a formulation, means the absolute stated value and other values proximal to the stated value that are sufficient to achieve a formulation that has an appropriate melting temperature, stability and dissolvability for use as a suppository. Appropriate melting temperatures, stability and dissolvability for a suppository, and methods for determining such properties of a formulation (e.g., suppository), are disclosed herein.

In contrast, the term "about" when used in the context of a temperature, means the absolute stated value and other values within a range of +/−2% of the stated value.

EXEMPLIFICATION

Example 1

Composition of Hydrocortisone Suppository Formulations

Several different prototypes of hydrocortisone formulations were made by formulating 90 mg of hydrocortisone acetate with one or more excipients into a 2 g suppository. The excipients tested included the polyethylene glycol bases PEG 300, PEG 1450, PEG 3350, PEG 6000, and PEG 8000, and the oleaginous bases WECOBEE® M, HYDRO-KOTE® C and HYDRO-KOTE® 112, WITEPSOL® H-15, and SUPPOCIRE® A, AS2, AML, and BS2. A subset of these initial prototypes also included either colloidal silicon dioxide or alginic acid as a suspending/dispersing agent.

Selection criteria were established. The top level criteria were melt point, stability and dissolution (release of the drug) (see Example 2 herein).

Second level criteria were hardness, consistency, suspension and appearance. Formulations that were too soft or brittle, showed signs of fracture or cracking, exhibited clumping or settling, or signs of water developing between the suppository and the shell were eliminated.

The final criterion was release from the casing. Formulations that were difficult to remove from the shells after cooling due to sticking were eliminated.

Upon evaluation, eight formulations, designated prototype numbers 36-43, were selected for further development and testing. The compositions of these eight formulations are indicated in Table 1. Each of these eight prototypes included colloidal silicon dioxide as an additive. Colloidal silicon dioxide is an adsorbent and is widely used in drugs, food, and even wine. This additive was important for preventing the hydrocortisone acetate from clumping and settling. In addition, the colloidal silicon dioxide facilitated keeping the hydrocortisone acetate in suspension, and promoted desired levels of consistency, dispersal, stability and release.

TABLE 1

Composition of Eight Prototype Hydrocortisone Formulations

| Prototype # | Composition |
| --- | --- |
| 36 | SUPPOCIRE ® A + colloidal silicon dioxide + HCA |
| 37 | SUPPOCIRE ® AS2 + colloidal silicon dioxide + HCA |
| 38 | SUPPOCIRE ® AML + colloidal silicon dioxide + HCA |
| 39 | SUPPOCIRE ® BS2 + colloidal silicon dioxide + HCA |
| 40 | WECOBEE ® M + colloidal silicon dioxide + HCA |
| 41 | HYDRO-KOTE ® 112 + colloidal silicon dioxide + HCA |
| 42 | HYDRO-KOTE ® 112 + colloidal silicon dioxide + HCA + BHT |
| 43 | HYDRO-KOTE ® 112 + HCA |

Example 2

Properties of Hydrocortisone Formulations

The eight prototype formulations selected in Example 1 were tested for melt point, stability and dissolution.

To assess melting point, each suppository containing one of the eight formulations was cut into three slices to produce a small, medium and large (large indicating that it fills the entire sample adaptor) slice, each of which was analyzed further to determine the drop point, which is the moment the first drop falls from the suppository. This was done to ensure that the size of the slice did not affect the drop point that was recorded. The slices were placed in a heating apparatus containing an oil bath and the temperature was increased steadily over time. At the moment the first drop fell from the suppository, both the temperature of the sample and the temperature of the oil bath were recorded. Then, the average sample temperature of the three drop points was calculated and used as the melting point for the formulation. Six of the prototypes were shown to have a melting point in the desired range of 37° C. to 39° C. after six weeks under storage conditions (see Table 2). The storage conditions included maintaining the formulations at a temperature of 25° C./60% relative humidity (RH) or 40° C./75% RH for 2, 4 or 6 weeks. The two formulations outside of the desired temperature range are highlighted in Table 2.

TABLE 2

Melting point data after 6 weeks in storage.

| Prototype composition | Melting temperature (° C.) Trial 1 | Melting temperature (° C.) Trial 2 | Melting temperature (° C.) Trial 3 | Melting temperature (° C.) Trial 4 | Melting temperature (° C.) Trial 5 | Average (° C.) |
| --- | --- | --- | --- | --- | --- | --- |
| HCA + CS + Wecobee | 37.50 | 39.00 | 39.00 | 38.50 | 40.50 | 38.90 |
| HCA + CS + Supp.AS2 | 39.00 | 38.25 | 38.50 | 40.50 | 39.00 | 39.05 |
| HCA + CS + Supp.A | 37.75 | 37.50 | 38.50 | 39.50 | 38.00 | 38.25 |
| HCA + CS + Witepsol H-15 | 37.25 | 36.00 | 38.00 | 36.00 | 39.00 | 37.25 |
| HCA + CS + Supp.AML | 38.25 | 38.00 | 38.25 | 37.00 | 37.50 | 37.80 |
| HCA + CS + Supp.BS2 | 39.50 | 38.50 | 39.00 | 37.50 | 39.00 | 38.70 |

TABLE 2-continued

Melting point data after 6 weeks in storage.

| Prototype composition | Melting temperature (° C.) Trial 1 | Melting temperature (° C.) Trial 2 | Melting temperature (° C.) Trial 3 | Melting temperature (° C.) Trial 4 | Melting temperature (° C.) Trial 5 | Average (° C.) |
|---|---|---|---|---|---|---|
| HCA + CS + Hydrokote 112 | 43.00 | 43.50 | 42.00 | 43.50 | 42.00 | 42.80 |
| HCA + CS + BHT + Hydrokote 112 | 42.50 | 42.50 | 41.00 | 44.50 | NA | 42.62 |

Surprisingly, all eight of the prototypes tested are stable at both 25° C. and 40° C. after two and four weeks under storage conditions (see Tables 3 and 4, respectively). A 90% recovery cut-off was used as an indicator of desirable stability. Failure to meet this 90% threshold by two of the formulations is most likely due to manual error in the sampling process, as each of the eight formulations is expected to have sufficient stability.

TABLE 3

Stability data at Week 2 for Eight Prototype Hydrocortisone Formulations.

| Prototype composition | Storage condition | % Recovery | % Impurity RRT 0.61 | RRT 1.08 | RRT 1.14 | RRT 1.19 |
|---|---|---|---|---|---|---|
| Wecobee M + Colloidal Silicon dioxide + Hydrocortisone acetate | 25° C./60% RH | 88.3 | 0.16 | 0.02 | 0.03 | 0.05 |
| | 40° C./75% RH | 99.3 | 0.17 | 0.03 | 0.04 | 0.06 |
| Suppocire A + Colloidal Silicon dioxide + Hydrocortisone acetate | 25° C./60% RH | 99.9 | 0.17 | 0.03 | 0.04 | 0.05 |
| | 40° C./75% RH | 101.8 | 0.17 | 0.03 | 0.04 | 0.05 |
| Suppocire AS2 + Colloidal Silicon dioxide + Hydrocortisone acetate | 25° C./60% RH | 99.6 | 0.17 | NA | NA | 0.05 |
| | 40° C./75% RH | 99.5 | 0.17 | NA | NA | 0.05 |
| Suppocire BS2 + Colloidal Silicon dioxide + Hydrocortisone acetate | 25° C./60% RH | 100.6 | 0.17 | 0.03 | 0.04 | 0.05 |
| | 40° C./75% RH | 100.7 | 0.17 | 0.03 | 0.04 | 0.05 |
| Suppocire AML + Colloidal Silicondioxide + Hydrocortisone acetate | 25° C./60% RH | 98.7 | 0.16 | 0.03 | 0.04 | 0.05 |
| | 40° C./75% RH | 101.6 | 0.16 | 0.03 | 0.04 | 0.05 |
| Witepsol H 15 + Colloidal Silicondioxide + Hydrocortisone acetate | 25° C./60% RH | 100.4 | 0.17 | 0.03 | 0.04 | 0.05 |
| | 40° C./75% RH | 100.8 | 0.17 | 0.03 | 0.04 | 0.04 |
| Hydrokote 112 + Colloidal Silicondioxide + Hydrocortisone acetate | 25° C./60% RH | 100.5 | 0.17 | 0.02 | 0.04 | 0.05 |
| | 40° C./75% RH | 100.3 | 0.16 | 0.03 | 0.04 | 0.05 |
| Hydrokote 112 + Colloidal Silicondioxide + Butylated hydroxy Toulene + Hydrocortisone acetate | 25° C./60% RH | 100.1 | 0.17 | 0.03 | 0.04 | 0.05 |
| | 40° C./75% RH | 101.1 | 0.17 | 0.03 | 0.04 | 0.05 |

TABLE 4

Stability data at Week 4 for Eight Prototype Hydrocortisone Formulations.

| Prototype composition | Storage condition | % Recovery | % Impurity | | | | | | | | Total Impurities |
|---|---|---|---|---|---|---|---|---|---|---|---|
| | | | RRT 0.422* | RRT 0.631 | RRT 0.797 | RRT 0.920 | RRT 1.175 | RRT 1.358 | RRT 1.484 | RRT 1.879 | |
| Suppocire A + Colloidal Silicon dioxide + Hydrocortisone acetate | 25° C./60% RH | 99.2 | 0.16 | ND | <LOQ | ND | <LOQ | <LOQ | 0.05 | <LOQ | 0.21 |
| | 40° C./75% RH | 103.9 | 0.18 | ND | <LOQ | ND | <LOQ | <LOQ | <LOQ | <LOQ | 0.18 |
| Suppocire AML + Colloidal Silicondioxide + Hydrocortisone acetate | 25° C./60% RH | 99.6 | 0.16 | ND | <LOQ | ND | <LOQ | <LOQ | 0.05 | <LOQ | 0.21 |
| | 40° C./75% RH | 102.1 | 0.17 | ND | <LOQ | ND | <LOQ | <LOQ | 0.05 | <LOQ | 0.22 |
| Suppocire AS2 + Colloidal Silicondioxide + Hydrocortisone acetate | 25° C./60% RH | 85.0 | 0.14 | ND | <LOQ | ND | <LOQ | <LOQ | <LOQ | <LOQ | 0.14 |
| | 40° C./75% RH | 100.3 | 0.18 | ND | <LOQ | ND | <LOQ | <LOQ | <LOQ | <LOQ | 0.18 |
| Suppocire BS2 + Colloidal Silicondioxide + Hydrocortisone acetate | 25° C./60% RH | 99.3 | 0.16 | ND | <LOQ | ND | <LOQ | <LOQ | <LOQ | <LOQ | 0.16 |
| | 40° C./75% RH | 101.1 | 0.17 | ND | <LOQ | ND | <LOQ | <LOQ | <LOQ | <LOQ | 0.17 |
| Wecobee M + Colloidal Silicondioxide + Hydrocortisone acetate | 25° C./60% RH | 96.6 | 0.17 | ND | <LOQ | ND | <LOQ | <LOQ | 0.05 | <LOQ | 0.22 |
| | 40° C./75% RH | 92.9 | 0.18 | ND | <LOQ | ND | <LOQ | <LOQ | 0.05 | <LOQ | 0.23 |
| Witepsol H 15 + Colloidal Silicondioxide + Hydrocortisone acetate | 25° C./60% RH | 99.6 | 0.16 | ND | <LOQ | ND | <LOQ | <LOQ | 0.05 | <LOQ | 0.21 |
| | 40° C./75% RH | 102.4 | 0.19 | ND | <LOQ | ND | <LOQ | <LOQ | 0.05 | <LOQ | 0.23 |
| Hydrokote 112 + Colloidal Silicondioxide + Hydrocortisone acetate | 25° C./60% RH | 99.7 | 0.16 | ND | <LOQ | ND | <LOQ | <LOQ | 0.05 | <LOQ | 0.21 |
| | 40° C./75% RH | 99.7 | 0.17 | ND | <LOQ | ND | <LOQ | <LOQ | 0.05 | <LOQ | 0.22 |

TABLE 4-continued

Stability data at Week 4 for Eight Prototype Hydrocortisone Formulations.

| Prototype composition | Storage condition | % Recovery | % Impurity | | | | | | | | Total Impurities |
|---|---|---|---|---|---|---|---|---|---|---|---|
| | | | RRT 0.422* | RRT 0.631 | RRT 0.797 | RRT 0.920 | RRT 1.175 | RRT 1.358 | RRT 1.484 | RRT 1.879 | |
| Hydrokote 112 + Colloidal Silicondioxide + BHT + Hydrocortisone acetate | 25° C./60% RH | 99.2 | 0.16 | ND | <LOQ | ND | <LOQ | <LOQ | 0.05 | <LOQ | 0.21 |
| | 40° C./75% RH | 99.6 | 0.16 | ND | <LOQ | ND | <LOQ | <LOQ | 0.05 | <LOQ | 0.21 |

The release of hydrocortisone acetate from each of the eight formulations was evaluated using a dissolution assay (see Example 3). For the dissolution assay, a media that contains glacial acetic acid and sodium lauryl sulfate (SLS), and which replicates the pH and environment of the rectum, was chosen.

The dissolution profile for each of the eight formulations after four weeks under storage conditions is shown in FIG. 1. SUPPOCIRE® A and SUPPOCIRE® AML shows the greatest percent released over a period of 300 minutes. In fact, SSUPPOCIRE® A and SUPPOCIRE® AML shows the greatest percent released up to the 100 minute mark. Based on the dissolution profile shown in FIG. 1, SUPPOCIRE® A and SUPPOCIRE® AML suggests ideal candidates for formulation.

Example 3

Exemplary Dissolution Assay for Hydrocortisone Formulations

The dissolution rates of hydrocortisone acetate in the formulations discussed in Example 2 and shown in FIG. 1 were determined by high-performance liquid chromatography (HPLC). Specifically, the samples were run on a reverse phase HPLC system with UV detection at 247 nanometer (nm).

A protocol for the assay is described below.
Materials and Equipment
Reagents and Materials
  Water, HPLC grade or equivalent
  Acetonitrile, HPLC grade or equivalent (ACN)
  a) Reference Materials
  Hydrocortisone USP reference standard or suitable equivalent characterized standard.
  b) Equipment
  HPLC system including:
    pump system capable of running a gradient
    autosampler capable of injecting 10 microliter (µL)
    UV absorbance detector capable of detection at 247 nm
    associated computer data acquisition system
  HPLC column: Agilent Eclipse Plus C18, 4.6×150 mm, 3.5 µm
  Microbalance capable of weighing a minimum of 25 mg
  Class A glassware
Safety Requirements
  General personal protection attire (lab coat, gloves, safety goggles, etc.) should be worn at all times.
Preparation of Solutions
  Alternate volumes of any preparation may be prepared by adjusting volumes and weights proportionately, with the exception that the weight of the standard preparations may not be reduced.

Preparation of Mobile Phase A
  Water is used as mobile phase A. Obtain 1L of Water. Degas
Preparation of Mobile Phase B
  ACN is used as mobile phase B. Obtain 1L of Acetonitrile. Degas
Preparation of Standard Solution
  If a stable standard is available for which standard agreement has already been demonstrated, preparation of fresh standards may be omitted. Accurately weigh and transfer approximately 25 mg±2.5 mg of Hydrocortisone reference standard material to a 250 milliliter (mL) volumetric flask. Dissolve in and dilute to volume with Acetonitrile and mix well. Prepare in duplicate (S1 and S2). Nominal concentration: 0.1 mg/mL of Hydrocortisone.
Dissolution Testing Procedure
  Weigh each suppository unit.
  Set up the dissolution bath to USP Apparatus I (Baskets).
  Equilibrate 900 mL of appropriate medium to 37° C. in each vessel used.
  Place one suppository unit in each basket and begin rotation at 50 RPM.
  Withdraw 5 mL from each vessel at 15, 30, 45, and 60 minutes (min).
  After 60 minutes, increase the paddle speed to 150 RPM and withdraw 5 mL at 90 minutes.
  Filter each sample through a 0.45 µm Nylon syringe filter discard the first 3 mL of the filtrate and use the rest for HPLC analysis.
Chromatographic Procedure
  HPLC Conditions
  Mobile Phase A: Water
  Mobile Phase B: Acetonitrile (ACN)
  Column: Agilent Eclipse Plus C18, 4.6×150 mm, 3.5µm
  Guard column: Frit
  Column Temperature: 30° C.
  Injection Volume: 10 µL
  Detection Wavelength: 247 nm
  Run Time: 45 minutes
  Flow Rate: 1.0 mL/minute
  Isocratic Flow: 50% A: 50% B
  Autosampler temperature: Ambient
  Hydrocortisone Acetate (Approx. RT): 3.6 minutes
Test Procedure
  Perform any number of equilibration injections of any standard prior to starting the analysis sequence. Do not re-inject from the vial used for equilibration injections after equilibration is complete. Clearly identify the equilibration injections as data not used. During analysis, it is preferable but not required to perform no more than one injection from a single vial.
  Determine system suitability at the beginning of the sequence with five injections of S1, two injections of S2 and at least one Diluent injection. System suitability injections may be performed in any order.

Sample injections should be bracketed by standard injections and no more than twelve samples should be run within a bracket. A standard that passes the criterion mentioned in Precision section, relative to one other standard preparation must be used as a bracketing standard.

System Suitability

Precision

Calculate the average peak area and % RSD obtained for the Hydrocortisone peak in each of the initial five standards (S1) injections. The % RSD must be ≤2.0.

For each bracketing standard throughout the run, calculate the % difference for the Hydrocortisone peak area in comparison to the average Hydrocortisone peak area from the five precision injections. The % difference for each bracketing standard must be ≤3.0.

Standard Agreement

Compare the average peak area for Hydrocortisone in the five system suitability injections of standard S1 with the peak area for Hydrocortisone in the two injections of standard S2. Agreement must be within 100.0±2.0%.

Standard agreement may be omitted from system suitability evaluation if a standard within its stability window has been shown to agree with another standard for Hydrocortisone.

Non-Interference

No significant interference greater than 0.05% of the Hydrocortisone average standard area (n=5) should be seen in an injection of Diluent.

Tailing Factor

The tailing factor for Hydrocortisone peak calculated for all the system suitability injections and bracketing standards must be ≤2.0.

Calculations and Reporting

Integration of Peaks

Set the minimum peak area for integration to not more than 0.05% of the average Hydrocortisone injector precision peak area. For all system suitability standard injections, integrate Hydrocortisone peak. Accurately integrate all the peaks in a sample chromatogram. It is permissible not to integrate peaks resulting from Diluent.

Standard Solution Concentration

Calculate the concentration of Hydrocortisone in the standard as follows:

$$\text{Concentration (mg/mL)} = \frac{W1 \times PF}{25 \text{ mL}}$$

Where: W1=weight of standard used to prepared the standard (mg)

PF*=purity factor of the reference standard taken from the certificate of analysis (in decimal form)

Calculation of Drug Substance Content

Calculate the % of Hydrocortisone in samples as follows:

$$\% = \frac{\left(\left(\frac{Area_{smpl}}{Area_{std}}\right) \times SC\right)}{\left(\frac{W1}{V1 - N \times 5}\right)} \times 100$$

Where: $Area_{smpl}$=Area of Urea in the sample $Area_{std}$=Area of Urea in the five precision standard injections SC=Standard concentration (mg/mL)

W1=Nominal weight of the Hydrocortisone in a unit, typically 90 mg

V1=Vessel volume (typically 900 mL)

| N | Time point (minutes) |
|---|---|
| 0 | 15 |
| 1 | 30 |
| 2 | 45 |
| 3 | 60 |
| 4 | 90 |

Example 4

Development and Characterization of Hydrocortisone Acetate Formulations Containing Colloidal Silicon Dioxide The studies herein include formulating different prototypes of hydrocortisone acetate suppositories and evaluating the prototypes for physical and chemical stability prior to refining the formulations based upon critical quality attributes (CQAs), such as melting point and the Active Pharmaceutical Ingredient (API) release profile. The final drug product that was chosen is a solid body of 2 g weight containing 90 mg of API in a fatty base adapted for introduction into the rectal orifice of the human body, which melts at about body temperature.

The studies herein have also evaluated aluminum shells and plastic shells for container closure system and found that both aluminum and plastic shells are compatible with the product based upon parameters such as ease of filling, visualization of the filled product, and product sticking to the shells. The current container closure system for the products are plastic suppository shells which accommodate up to 2 grams of product.

The selection of base is one of the important aspects in the development of the suppositories. The selected base can influence the mechanism of action. Initially, placebo prototypes 1-10 (compositions shown in Table 5) were made to evaluate the aesthetics and ease of filling. The bases were weighed according to the composition and melted. The colloidal silicon dioxide was then added to the melted base and solubilized (for prototypes with colloidal silicon dioxide). The melted preparation was then poured into the shells. During the filling operation, it was observed that prototypes 1, 2, and 3 were very viscous and difficult to fill into the shells even at higher temperatures such as 80 degrees Celsius (° C.). Conversely, prototypes 4-10 were less viscous when compared to prototypes 1, 2, and 3 and were easy to fill into the shells at a temperature of 50° C. The shells were sealed and the suppositories were allowed to solidify. After a few days, the suppositories were evaluated for aesthetics. Prototypes 1, 2, and 3 exhibited cracks in the suppositories whereas prototypes 4-10 did not exhibit any cracks.

TABLE 5

Compositions of Various Placebo Prototypes (% w/w).

| Material | Prototype 1 | 2 | 3 | 4 | 5 | 6 | 7 | 8 | 9 | 10 |
|---|---|---|---|---|---|---|---|---|---|---|
| PEG 300 | 60 |  | 10 |  |  |  |  |  |  |  |
| PEG 8000 | 40 |  |  |  |  |  |  |  |  |  |
| PEG 1450 |  | 30 | 65 |  |  |  |  |  |  |  |
| PEG 3350 |  | 70 | 25 |  |  |  |  |  |  |  |
| Suppocire AML |  |  |  | 99.3 |  |  |  |  |  |  |
| Suppocire A |  |  |  |  | 99.3 |  |  |  |  |  |
| Suppocire AS2 |  |  |  |  |  | 99.3 |  |  |  |  |
| Suppocire BS2 |  |  |  |  |  |  | 99.3 |  |  |  |
| Witepsol H-15 |  |  |  |  |  |  |  | 99.3 |  |  |
| Wecobee M |  |  |  |  |  |  |  |  | 99.3 |  |
| Hydrokote 112 |  |  |  |  |  |  |  |  |  | 99.3 |
| Colloidal silicon dioxide |  |  |  | 0.7 | 0.7 | 0.7 | 0.7 | 0.7 | 0.7 | 0.7 |

The Table 5 observations and previous published studies indicate that PEG-based suppositories can cause irritancy. Thus, prototypes 1, 2, and 3 were eliminated from further study. Building upon the data that was provided in Table 5, active formulations using hydrocortisone acetate (90 mg) were prepared. The compositions of active prototypes 11-17 are shown in Table 6. The active prototypes were kept in stability chambers at two conditions: 1) 25° C./60% relative humidity (RH); and 2) 40° C./75% RH, for one month prior to the stability study that were used to evaluate physical and chemical stability.

The suppositories in Table 6 were evaluated for physical stability such as cracks within the suppositories, discoloration and feel. Prototypes 11-17 did not exhibit cracks within the suppositories, discoloration or unsatisfactory feel. The suppositories in Table 6 were then stored at 40° C./75% RH and allowed to solidify at room temperature for further evaluations.

Prototypes 11-17 were next evaluated for Critical Quality Attributes (CQAs) such as melting point (as the mechanism of action for fat based suppositories is melting), and release profile for the API in order to identify the lead formulation. Table 7 shows the melting point data for prototypes 11-17.

TABLE 6

Compositions of Active Prototypes.

| Material | 11 % w/w | 12 % w/w | 13 % w/w | 14 % w/w | 15 % w/w | 16 % w/w | 17 % w/w |
|---|---|---|---|---|---|---|---|
| Suppocire AML | 94.8 |  |  |  |  |  |  |
| Suppocire A |  | 94.8 |  |  |  |  |  |
| Suppocire AS2 |  |  | 94.8 |  |  |  |  |
| Suppocire BS2 |  |  |  | 94.8 |  |  |  |
| Witepsol H-15 |  |  |  |  | 94.8 |  |  |
| Wecobee M |  |  |  |  |  | 94.8 |  |
| Hydrokote 112 |  |  |  |  |  |  | 94.8 |
| Colloidal silicon dioxide | 0.7 | 0.7 | 0.7 | 0.7 | 0.7 | 0.7 | 0.7 |
| Hydrocortisone acetate | 4.5 | 4.5 | 4.5 | 4.5 | 4.5 | 4.5 | 4.5 |

TABLE 7

Melting Point Data for the Active Prototypes.

| Prototype | Melting temperature (° C.) Trial 1 | Melting temperature (° C.) Trial 2 | Melting temperature (° C.) Trial 3 | Melting temperature (° C.) Trial 4 | Melting temperature (° C.) Trial 5 | Average |
|---|---|---|---|---|---|---|
| 11 | 38.25 | 38.00 | 38.25 | 37.00 | 37.50 | 37.80 |
| 12 | 37.75 | 37.50 | 38.50 | 39.50 | 38.00 | 38.25 |
| 13 | 39.00 | 38.25 | 38.50 | 40.50 | 39.00 | 39.05 |
| 14 | 39.50 | 38.50 | 39.00 | 37.50 | 39.00 | 38.70 |

TABLE 7-continued

Melting Point Data for the Active Prototypes.

| Prototype | Melting temperature (° C.) Trial 1 | Melting temperature (° C.) Trial 2 | Melting temperature (° C.) Trial 3 | Melting temperature (° C.) Trial 4 | Melting temperature (° C.) Trial 5 | Average |
|---|---|---|---|---|---|---|
| 15 | 37.25 | 36.00 | 38.00 | 36.00 | 39.00 | 37.25 |
| 16 | 37.50 | 39.00 | 39.00 | 38.50 | 40.50 | 38.90 |
| 17 | 43.00 | 43.50 | 42.00 | 43.50 | 42.00 | 42.80 |

Table 7 shows that the average melting point of prototypes 11-16 is between approximately 37° C. to 39° C. The average melting point of prototype 17 was found to be slightly higher at approximately 43° C. As the melting point of all the prototypes studied was found to be quite close, the API release profile was next evaluated to identify the lead formulation from the group of prototypes.

Example 5

Development of a Dissolution Method for Testing Suppository Formulations

In order to assess the API release profile from the prototypes in Example 4 to identify a lead formulation, a robust dissolution method was developed. Solubility studies were performed on the API for the selection of dissolution media. For these studies, the active concentration of the dissolution media was 0.1 milligrams per milliliter (mg/mL). The results of the solubility of 0.1 mg/mL hydrocortisone acetate in various dissolution medias is shown in Table 8.

TABLE 8

Solubility of API (0.1 mg/mL) in Various Dissolution Media.

| Dissolution media | % Solubility API |
|---|---|
| 0.5% Tween 80 | 12.4 |
| 3% Tween 80 | 20.6 |
| Phosphate buffer pH 7.2 | 4.1 |
| 0.5% w/v SLS | 57.6 |
| 3% w/v SLS | 73.5 |
| 5% w/v SLS | 99.7 |
| 10% w/v SLS | 98.7 |

SLS = sodium lauryl sulfate

According to USP guidelines (on sink conditions) the solubility needs to be at least 3 times the proposed active concentration. As shown in Table 8, sodium lauryl sulfate (SLS) achieved the highest percent solubility of the API (hydrocortisone acetate). The studies next turned to the use of higher hydrocortisone acetate concentrations (0.3 mg/mL). The solubility of 0.3 mg/mL hydrocortisone acetate in various dissolution media is shown in Table 9.

TABLE 9

Solubility of hydrocortisone acetate (0.3 mg/mL) in SLS Dissolution Media.

| Dissolution media | % Solubility |
|---|---|
| 5% w/v SLS | 98.9 |
| 10% w/v SLS | 99.3 |

As shown in Table 9, the solubility percent of 0.3 mg/mL hydrocortisone acetate in SLS still remained high. In order to avoid ionization of the hydrocortisone acetate in the dissolution media, a buffer of pH 5.0 was used in combination with 5% w/v SLS. The final composition of the dissolution media was 5% w/v SLS:acetate buffer (pH 5.0) in 70:30 combination with the pH of the final combination adjusted to 6.8-7.0. The average recovered solubility of 0.3 mg/mL hydrocortisone acetate in the proposed dissolution media was 98.4%.

According to the results shown in Tables 8 and 9, the optimized dissolution parameters include:
Dissolution media: 5% w/v SLS: acetate buffer pH 5.0 (70:30) final pH adjusted to 6.8-7.0.
USP Apparatus II (Paddles).
Dissolution volume: 900 mL.
Rotations per minute (RPM): 50.
Temperature: 37° C.
Time points: 15 min, 30 min, 60 min, 90 min, 120 min, 180 min, and 360 min.

Prototypes 11-17 were then tested for hydrocortisone acetate release under the optimized dissolution parameters obtained from Table 9. Table 10 shows the hydrocortisone acetate release profile of prototypes 11-17.

TABLE 10

Percent Hydrocortisone Acetate Released with Respect to Time for the Prototypes.

| | % API released after respective time (min) | | | | | | |
|---|---|---|---|---|---|---|---|
| Prototype | 15 | 30 | 60 | 90 | 120 | 180 | 360 |
| 11 | 9.66 | 22.13 | 42.09 | 58.92 | 72.73 | 89.39 | 98.82 |
| 12 | 6.76 | 9.55 | 15.29 | 21.20 | 27.00 | 35.70 | 52.31 |
| 13 | 7.23 | 14.96 | 31.93 | 46.17 | 57.96 | 73.89 | 89.76 |
| 14 | 1.32 | 4.25 | 11.05 | 15.68 | 18.99 | 23.72 | 30.22 |
| 15 | 13.25 | 24.27 | 37.93 | 49.35 | 62.32 | 77.53 | 90.42 |
| 16 | 1.35 | 3.00 | 4.89 | 6.33 | 7.52 | 9.35 | 13.39 |
| 17 | 6.39 | 16.02 | 42.09 | 68.88 | 86.12 | 93.51 | 94.10 |

Figure 2:
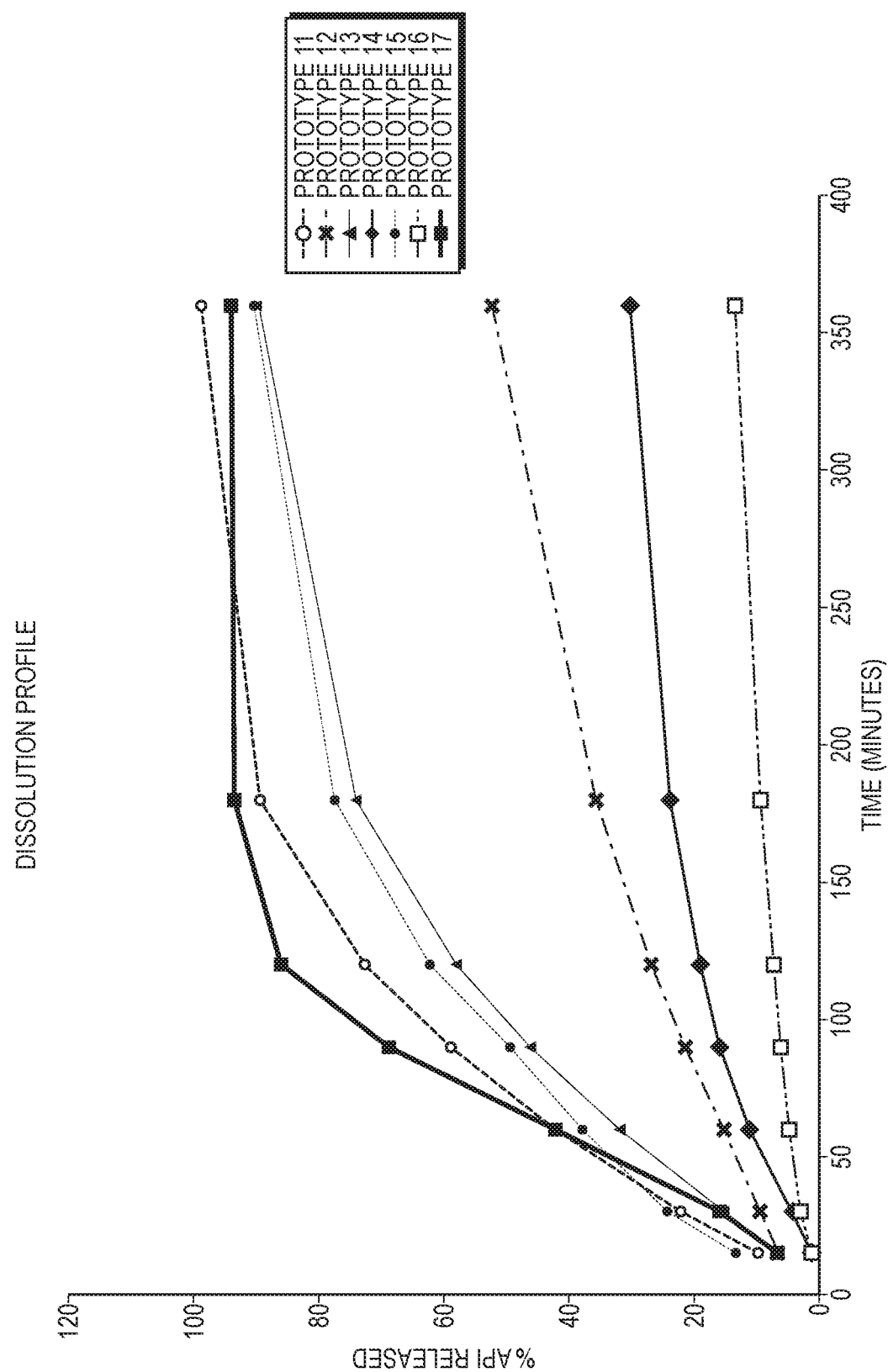
FIG. 2 is a graph showing the hydrocortisone acetate release profile of seven prototype hydrocortisone formulations.

As shown in Table 10, prototypes 11, 13, 15, and 17 were identified as having the best dissolution. The dissolution profile for each of the prototypes 11-17 is shown in FIG. 2. Prototypes 11, 13, 15, and 17 show the greatest percent of hydrocortisone acetate released over a period of 350 minutes. In fact, prototypes 11, 13, 15, and 17 show the greatest percent of hydrocortisone acetate released at 150 minutes. Based on the hydrocortisone acetate release profile for each of the prototypes shown in FIG. 2, prototypes 11, 13, 15, and 17 were selected for lead formulation.

Based on the melting point profile (Table 7), release profile (Table 10) and FIG. 2, prototypes 11, 13, 15, and 17 were identified as the lead formulations. However, prototypes 13 and 17 were removed from the studies by taking into consideration the compendial status of the base used in prototype 17 and the high melting point of prototype 13. Thus, prototypes 11 and 15 were selected as the top two formulations (Table 11).

TABLE 11

Composition of the Lead and Backup Formulations.

| Prototype | Ingredient | Composition (% w/w) |
|---|---|---|
| 11 | Suppocire AML | 94.8 |
|  | Colloidal silicon dioxide | 0.7 |
|  | Hydrocortisone acetate | 4.5 |
| 15 | Witepsol H-15 | 94.8 |
|  | Colloidal silicon dioxide | 0.7 |
|  | Hydrocortisone acetate | 4.5 |

Taking the composition of WITEPSOL® H-15 base (contains hydrogenated coco-glycerides which might have polymorphism issues) into consideration, prototype 15 was selected as the backup formulation. Thus, the prototype 11 composition containing SUPPOCIRE® AML, base (Table 12) was selected as the lead formulation.

TABLE 12

Composition of the Lead Formulation.

| Ingredient No. | Ingredient | Grade | Function | Composition per 2 gram suppository | Maximum IIG limit |
|---|---|---|---|---|---|
| 1 | Hydrocortisone acetate | USP | API | 90 mg | NA |
| 2 | Suppocire AML | USP/NF/JP | Base | 1896 mg | 1920 mg |
| 3 | Colloidal silicon dioxide | NF | Suspending agent | 14 mg | 14 mg |

IID = United States Food & Drug Administration's "Inactive Ingredient Guide"
USP = United States Pharmacopeia
NF =
JPE =
NA = not applicable The results from these studies led to the selection of the SUPPOCIRE® AML active prototype formulation as the lead formulation based on its superior physical and dissolution properties. The selected lead formulation includes hydrocortisone acetate 90 mg, colloidal silicon dioxide 14 mg and SUPPOCIRE® AML 1896 mg, which provides a suppository with a total weight of 2 g. This lead formulation was then subjected to physical and chemical stability, and dissolution studies.

Physical and Chemical Stability Studies of the Lead Formulation

The selected lead formulation (prototype 11: hydrocortisone acetate 90 mg, colloidal silicon dioxide 14 mg and SUPPOCIRE® AML 1896 mg) was subjected to physical and chemical stability studies. The study employed two storage conditions in order to demonstrate compatibility with the selected excipients and to give confidence that the formulations are appropriate for longer storage. The conditions include:

25±2° C. I 60±5% RH (relative humidity)=standard storage conditions

40±2° C. I 75±5% RH (relative humidity)=accelerated storage conditions

The results of the physical and chemical stability studies showing the assay and impurity results for SUPPOCIRE® AML active prototypes under storage conditions (standard and accelerated) are summarized in Table 14.

TABLE 13

Assay and Impurities Results for SUPPOCIRE® AML-Containing Prototype (Hydrocortisone Acetate 90 mg and Colloidal Silicon Dioxide 14 mg).

| Peak name | T = 0 sample % L.C. | T = 1 month @ 25/60 % L.C. | T = 1 month @ 40/75 % L.C. | T = 2 month @ 25/60 % L.C. | T = 2 month @ 40/75 % L.C. | T = 3 month @ 25/60 % L.C. | T = 3 month @ 40/75 % L.C. |
|---|---|---|---|---|---|---|---|
| Hydrocortisone acetate | 98.6 | 97.5 | 98.4 | 96.9 | 101.3 | 97.3 | 99.8 |
| RRT 0.601 | ND | ND | ND | ND | ND | <LOQ | <LOQ |
| RRT 0.623 | 0.18 | 0.16 | 0.17 | 0.16 | 0.19 | 0.15 | 0.16 |
| RRT 0.823 | ND | ND | ND | ND | ND | 0.08 | <LOQ |
| RRT 0.860 | <LOQ | <LOQ | 0.05 | <LOQ | 0.06 | <LOQ | <LOQ |
| RRT 0.889 | ND | ND | ND | ND | ND | <LOQ | <LOQ |
| RRT 0.937 | <LOQ | <LOQ | <LOQ | <LOQ | <LOQ | <LOQ | <LOQ |
| RRT 0.968 | ND | ND | ND | ND | ND | <LOQ | <LOQ |
| RRT 1.075 | <LOQ | <LOQ | <LOQ | <LOQ | <LOQ | <LOQ | <LOQ |

TABLE 13-continued

Assay and Impurities Results for SUPPOCIRE ® AML-Containing
Prototype (Hydrocortisone Acetate 90 mg and Colloidal Silicon Dioxide 14 mg).

| Peak name | T = 0 sample % L.C. | T = 1 month @ 25/60 % L.C. | T = 1 month @ 40/75 % L.C. | T = 2 month @ 25/60 % L.C. | T = 2 month @ 40/75 % L.C. | T = 3 month @ 25/60 % L.C. | T = 3 month @ 40/75 % L.C. |
|---|---|---|---|---|---|---|---|
| RRT 1.145 | <LOQ | <LOQ | 0.05 | 0.05 | <LOQ | <LOQ | <LOQ |
| RRT 1.186 | 0.05 | 0.05 | <LOQ | 0.06 | 0.05 | <LOQ | <LOQ |
| RRT 1.332 | <LOQ | <LOQ | <LOQ | <LOQ | <LOQ | <LOQ | <LOQ |
| Total Impurities | 0.23 | 0.21 | 0.27 | 0.27 | 0.30 | 0.23 | 0.16 |

% L.C. = % Label Claim
RRT = Relative Retention Time
ND = not detected
<LOQ = Less than Limit Of Detection The results from the initial and one month through three month stability studies for the lead prototype (SUPPOCIRE® AML with hydrocortisone acetate 90 mg and colloidal silicon dioxide 14 mg) shows negligible amounts of total impurities after three months of storage (Table 13). These studies demonstrate that the lead formulation remains stable for at least three months under the conditions tested.

Dissolution Studies

The selected lead formulation 11 (hydrocortisone acetate 90 mg, colloidal silicon dioxide 14 mg and SUPPOCIRE® AML 1896 mg) was next subjected to dissolution studies (Table 14). Samples stored at both 25° C./60% RH and 40° C./75% RH were subjected to the dissolution testing. Samples stored at 25° C./60% RH were subjected to dissolution testing at initial (Time (T)=O), 1 month (T=1) and 2 months (T=2) of storage. Samples stored at both 25° C./60% RH and 40° C./75% RH were subjected to testing at 3 months (T=3) and 7 months (T=7) of storage.

consistent even after 7 months of storage at standard storage conditions (25° C./60% RH). However, storage at accelerated conditions (40° C./75% RH) after 7 months resulted in a decrease of hydrocortisone acetate release from the lead formulation.

These results led to the selection of a SUPPOCIRE® AML active prototype formulation with hydrocortisone acetate 90 mg and colloidal silicon dioxide 14 mg as the lead formulation for the hydrocortisone acetate suppository studies based on its desirable properties, as indicated by the assay results (Table 13) and dissolution release profile (Table 14).

Example 6

Hydrocortisone Acetate (90 mg) Suppository Specification and Dissolution Profile The specification and dissolution profile for the 2 gram suppository containing 90 mg of hydrocortisone acetate and colloidal silicon dioxide (prototype 11) is shown in Table 15.

TABLE 14

Dissolution Profiles for SUPPOCIRE ® AML Formulation with Hydrocortisone
Acetate 90 mg and Colloidal Silicon Dioxide 14 mg (T = 0 to T = 7).
Active with Suppocire AML (Average of n = 6 vessels)

| Time (Min) | Initial | 1 month | 2 month | 3 month 25° C./60% RH | 3 month 40° C./75% RH | 7 month 25° C./60% RH | 7 month 40° C./75% RH |
|---|---|---|---|---|---|---|---|
| 15 | 11.09 | 6.97 | 8.46 | 8.58 | 7.52 | 6.87 | 7.48 |
| 30 | 21.83 | 18.56 | 22.94 | 20.50 | 14.09 | 19.24 | 12.46 |
| 60 | 45.49 | 37.62 | 45.78 | 38.34 | 25.17 | 39.33 | 18.48 |
| 90 | 63.71 | 50.93 | 63.10 | 54.69 | 40.39 | 55.92 | 21.93 |
| 120 | 78.29 | 62.74 | 76.09 | 66.41 | 46.35 | 69.68 | 25.64 |
| 180 | 93.22 | 83.14 | 90.59 | 86.67 | 50.79 | 87.42 | 32.03 |
| 360 | 99.01 | 97.49 | 98.16 | 98.53 | 68.42 | 100.30 | 49.05 |

The results of the dissolution studies (Table 14) show that the dissolution profile for hydrocortisone acetate remains

TABLE 15

Two Gram Suppository (Hydrocortisone Acetate 90 mg) Specification and
Dissolution Profile.

| Test | Method | Specifications | Initial | 30 Day |
|---|---|---|---|---|
| Film Seal Integrity | Visual | Film Tightly Sealed | Pass | Pass |
| Appearance | Visual | White to off white bullet shaped suppository free from visible contamination and cracks | Pass | Pass |

TABLE 15-continued

Two Gram Suppository (Hydrocortisone Acetate 90 mg) Specification and Dissolution Profile.

| Test | Method | Specifications | Initial | 30 Day |
|---|---|---|---|---|
| Melting Temperature | USP <741> | Report Value | 36.5 C. | 35.9 C. |
| Assay | DOP-QC-224 | 90.0%-110.0% | 100.70% | 100.10% |
| Related Substances | DOP-QC-224 | | | |
| Hydrocortisone | | Report % | 0.25% | 0.23% |
| 17-dehydro-21 hydroxy hydrocortisone | | Report % | 0.08% | 0.05% |
| Individual Unknown impurities | | Report % and RRT | <0.05% | RRT 0.84, 0.03% RRT 0.93, 0.03% |
| Total Unknown impurities | | Report % | <0.05% | 0.05% |
| Dissolution | DOP-QC-225 | | | |
| 15 minutes | | Report % | 12.0% | 6.7% |
| 30 minutes | | Report % | 21.9% | 16.8% |
| 60 minutes | | Report % | 34.9% | 30.7% |
| 90 minutes | | Report % | 48.6% | 40.0% |
| 120 minutes | | Report % | 59.0% | 48.9% |
| 180 minutes | | Report % | 80.8% | 54.5% |
| 360 minutes | | Report % | 97.3% | 82.4% |
| 375 minutes | | Report % | 98.3% | 99.8% |
| Total Aerobic Plate Count | DOP-QC-114 USP <61> | NMT 2000 cfu/g | NMT 10 | N/A |
| Total Combined Yeast and Mold | DOP-QC-114 USP <61> | NMT 2000 cfu/g | NMT 10 | N/A |

The hydrocortisone acetate (90 mg) suppository was packaged in 2 gram polyethylene/polyvinyl chloride (PE/PVC) suppository shells and subjected to standard CQAs for 60 days under 40° C./75% RH storage conditions. As shown in Table 15, the appearance, melting temperature and stability of the 2 g suppository hydrocortisone acetate 90 mg remained constant and virtually unchanged after 60 days of storage under accelerated conditions (40° C./75% RH). Total impurities that were generated over a period of 60 days remained negligible (<0.05%) under accelerated storage conditions (40° C./75% RH). Moreover, the dissolution studies under our standard protocol have also shown that the 2 g suppository releases at least about 80% of the hydrocortisone acetate at about 180 minutes following exposure to dissolution media comprising 5% w/v sodium lauryl sulfate:acetate buffer pH 5.0 (70:30) final pH adjusted to 6.8-7.0. At about 360 minutes following exposure to dissolution media comprising 5% w/v sodium lauryl sulfate:acetate buffer pH 5.0 (70:30) final pH adjusted to 6.8-7.0, the 2 g suppository releases at least about 97% of the hydrocortisone acetate. Specifications and Analytical Procedures for Examples 4 to 6

The CQAs are melting point, release profile, color, appearance, content uniformity, assay and dissolution study. The specifications for the CQAs are shown in Table 16.

TABLE 16

Specifications for the CQAs.

| Test | Limits | Method |
|---|---|---|
| A. Appearance | White to off-white no cracks within suppositories | Visual |
| B. Hydrocortisone Acetate Identification* | HPLC RT value in sample corresponds to hydrocortisone acetate reference standard | M-CCO-LC-002 |
| C. Assay | 98.0-102.0% of label claim | M-CCO-LC-002 |
| D. Within Batch Process Homogencity (beginning, middle, and end samples)* | Assay range: 90.0%-110.0% RSD NMT 6% | M-CCO-LC-002 |
| E. Dissolution | Report Results | M-CCO-LC-001 |
| F. Degradation Products: Individual Unknown Impurities Total Impurities | Report Results | M-CCO-LC-002 |
| G. Melting Point | Reports Results | USP <741> |
| H. Content Uniformity* | The acceptance criteria per USP<905> is AV (Acceptance Value) is NMT 15.0% (n = 10). IF n = 10 fails to meet the criteria, then Content Uniformity (CU) will be performed on additional 20 units (stage-2) and the AV value is calculated for a total of 30 units. The acceptance criteria is AV NMT 15.0% (n = 30). | M-CCO-LC-002 |

*= Tests will be performed only on intial T-zero samples.
NMT = No More Than

Analytical Procedures

General experimental techniques for Examples 4-6 can be accomplished by the methods described herein.

General Dissolution Method: M-CCO-LC-001 and DOP-QC-225
HPLC Column: Agilent Eclipse Plus C18, 4.6×150 mm, 3.5 µm.
Preparation of Dissolution Media: Prepared 5% w/v sodium lauryl sulfate: acetate Buffer pH 5.0 (70:30), and adjusted the final pH to 6.8.
Preparation of Standard Solution: Prepared a standard solution containing about 0.1 mg/mL hydrocortisone reference standard in dissolution medium.
Preparation of Samples: Hydrocortisone Acetate Suppository samples were subjected to dissolution experiment and sampled at specified time points as described in the test method.
General Assay Method: M-CCO-LC-002 and DOP-QC-224
HPLC Column: Agilent Eclipse Plus C18, 4.6×150 mm, 3.5 µm.
Preparation of Standard Solution: Prepared a standard solution containing about 0.18 mg/mL hydrocortisone acetate reference standard in acetonitrile.
Preparation of Samples: Prepared sample solutions containing about 0.18 mg/mL hydrocortisone acetate sample in acetonitrile.
Dissolution Method
Reagents and Materials
Water, HPLC grade or equivalent
Acetonitrile, HPLC grade or equivalent (ACN)
Sodium Acetate Trihydrate, ACS grade
Sodium Lauryl Sulfate (SLS), NF grade
2 Normal (N) Acetic acid
5N Sodium hydroxide (NaOH), ACS grade
Reference Materials
Hydrocortisone Acetate, United States Pharmacopeia (USP) reference standard or suitable equivalent characterized standard.
Equipment
HPLC system including:
  Pump system capable of running a gradient
  Auto sampler capable of injecting 10 µL
  UV absorbance detector capable of detection at 247 nm
  Associated computer data acquisition system
HPLC column: Agilent Eclipse Plus C18, 4.6×150 mm, 3.5 µm
Microbalance capable of weighing a minimum of 25 mg
Class A glassware
0.45 µm Polytetrafluoroethylene (PTFE) syringe filter
Spring Style Capsule Sinker, 316 SS, QLA, Part# CAPWST-31
Preparation of Mobile Phase A
Water is used as mobile phase A. Obtain 1 L of Water. Degas.
Preparation of Mobile Phase B
ACN is used as mobile phase B. Obtain 1 L of Acetonitrile. Degas.
Note: Premixed solution of (50:50) ACN:Water can also be used as mobile phase.
Preparation of Standard Solution
If a stable standard is available for which standard agreement has already been demonstrated, preparation of fresh standards may be omitted. Accurately weigh and transfer approximately 25±2.5 mg of Hydrocortisone Acetate reference standard material to a 250 mL volumetric flask. Add 250 ml of ACN. Heat it in oven at 70° C. for 30 minutes and sonicate to dissolve. Cool it to room temperature. Dilute to volume with dissolution media and mix well. Nominal concentration: 0.1 mg/mL of Hydrocortisone Acetate.

Preparation of 5% weight/volume (w/v) Sodium Lauryl Sulfate
Dissolve 50 g of Sodium Lauryl Sulfate in 1 L of water. Heat the solution if necessary to ensure dissolution. Scale as necessary.
Preparation of Acetate buffer pH 5.0
Dissolve 20 g of Sodium Acetate trihydrate in 4 L of water. Add 26 mL of 2N acetic acid. Adjust the pH to 5±0.05 with 2N acetic acid. Scale as necessary.
Dissolution Media
For each liter of dissolution media, combine 700 mL of 5% w/v SLS and 300 mL of Acetate buffer pH 5.0. Adjust the pH to 6.8±0.05 with 5N NaOH. Sonicate for 30 min.
Dissolution Testing Procedure
  Weigh each suppository unit.
  Set up the dissolution bath to USP Apparatus 2 (Paddles).
  Equilibrate 900 mL of dissolution media to 37° C. in each vessel used.
  Place one suppository unit in each sinker, drop it in the vessel and begin rotation at 50 rotations per minute (RPM).
  Withdraw 5 mL from each vessel at 15, 30, 60, 90, 120, 180 and 360 minutes.
  After 360 minutes, increase the speed to 150 RPM and withdraw 5 mL after 15 min.
  Filter each sample through a 0.45 µL PTFE syringe filter discard the first 3 mL of the filtrate and use the rest for HPLC analysis.
Note: Samples are stable for 4 days at room temperature.
Chromatographic Procedure
Mobile Phase A: Water
Mobile Phase B: Acetonitrile
Column: Agilent Eclipse Plus C18, 4.6×150 mm, 3.5 xm
Guard column: Frit
Column Temperature: 30±3° C.
Injection Volume: 10 µm
Detection Wavelength: 247 nm
Run Time: 10 minutes
Flow Rate: 1.0±0.1 mL/minute
Isocratic Flow: 50% A: 50% B(±10%)
Auto sampler temperature: Ambient
Retention Time: Approximately 3.6 minutes for Hydrocortisone Acetate
Assay Method
Reagents and Materials
Water, HPLC grade or equivalent
Acetonitrile, HPLC grade or equivalent (ACN)
Triflouroacetic Acid, HPLC grade or equivalent (TFA)
Reference Materials
Hydrocortisone Acetate USP reference standard or suitable equivalent characterized standard.
Equipment
HPLC system including:
  Pump system capable of running a gradient
  Auto sampler capable of injecting 10
  UV absorbance detector capable of detection at 247 nm
  Associated computer data acquisition system
  column heater capable of heating to 30° C.
HPLC column: Agilent Eclipse Plus C18, 4.6×150 mm, 3.5 µm
Microbalance capable of weighing a minimum of 36 mg
Class A glassware
0.20 µm PTFE syringe filter
Preparation of Mobile Phase A (0.1% TFA in Water)
Obtain 1 L of Water. Add 1 mL of TFA. Mix well and degas.
Preparation of Mobile Phase B (0.1% TFA in ACN)
Obtain 1 L of ACN. Add 1 mL of TFA. Mix well and degas.

Preparation of Standard Solution

If a stable standard is available for which standard agreement has already been demonstrated, preparation of fresh standards may be omitted. Accurately weigh and transfer approximately 36±3 mg of Hydrocortisone Acetate reference standard material to a 200 mL volumetric flask. Add 150 ml of ACN. Sonicate if necessary. Dilute to volume with ACN and mix well.

Nominal concentration: 0.18 mg/mL of Hydrocortisone Acetate.

Stability of Standard: Standard solution is stable for 11 days at room temperature.

Preparation of Samples for Assay

Accurately weigh 5 units of suppositories and transfer into a 1000 mL volumetric flask and add 500 mL of Acetonitrile using an appropriate graduated cylinder. Place a stir bar and heat it in a water bath at 70° C. for 30 minutes at 700 RPM. Remove the stir bar and cool to room temperature. Mix well. Filter 10 mL of sample through a 0.20 µm PTFE syringe filter to a 10 mL plastic syringe. Discard the first 3 mL and collect the filtrate to a scintillation vial. Pipette 5.0 mL of the filtrate to a 25 mL volumetric flask and dilute to volume with ACN. Mix well.

Nominal concentration: 0.18 mg/mL of Hydrocortisone Acetate.

Stability of Sample: Sample solution is stable for 6 days at room temperature.

Preparation of Samples for Content Uniformity

Accurately weigh out a unit of suppository and transfer into a 500 mL volumetric flask and approximately add 400 mL of Acetonitrile. Place a stir bar in the flask and heat it in a water bath at 70° C. for 30 minutes at 700 RPM. Remove the stir bar and cool to room temperature. Dilute to volume with Acetonitrile and mix well. Filter 5 mL of sample through a 0.20 µm PTFE syringe filter to a 5 mL plastic syringe. Discard the first 3 mL before collecting sample for analysis.

Nominal concentration: 0.18 mg/mL of Hydrocortisone Acetate.

Stability of Sample: Sample Solutions is stable for 6 days at room temperature.

HPLC Conditions

Mobile Phase A: 0.1% TFA in Water
Mobile Phase B: 0.1% TFA in ACN
Column: Agilent Eclipse Plus C18, 4.6×150 mm, 3.5 µm
Guard column: Aquasil C18 or equivalent
Column Temperature: 30° C.
Injection Volume: 10 µm
Detection Wavelength: 247 nm
Run Time: 35 minutes
Flow Rate: 1.0 mL/minute
Auto sampler temperature: Ambient
Gradient program:

| Time (Minutes) | % A | % B |
| --- | --- | --- |
| 0 | 75 | 25 |
| 20 | 25 | 75 |
| 25 | 25 | 75 |
| 25.1 | 75 | 25 |
| 35 | 75 | 25 |

Retention Time: Approximately 10.7 minutes for Hydrocortisone Acetate

USP <741>: U.S. Pharmacopeia Monograph 741—Melting Range or Temperature

USP <905>: U.S. Pharmacopeia Monograph 905—Uniformity of Dosage Units

USP <61>: U.S. Pharmacopeia Monograph 61—Microbial Examination of Nonsterile Products Example 7

Manufacturing Process for Hydrocortisone Acetate Suppository Formulation

The lead formulation was manufactured (both active and placebo) and subjected to stability studies at two different conditions: 1) 25° C./60% RH; and 2) 40° C./75% RH.

Preparation of the base: The stainless steel vessel identification number and tare weight was recorded. Into the vessel, was add the weighed amount of base and begin melting the base using a hot stir plate and water bath, low shear sweep/side scrape mixing (hand mix was used in the lab for small scale operations) until all the base was completely melted. The temperature was maintained at 55±5° C. ($T_f$).

Addition of colloidal silicon dioxide: A silverson mixer (or similar homogenizer) was set up. The required amount of colloidal silicon dioxide was weighed and added to the melted base. The colloidal silicon dioxide was then allowed to hydrate by mixing using a square shape mesh. The mixing speed was maintained between 3000-3500 RPM. The temperature was maintained at 55±5° C. ($T_f$).

Addition of hydrocortisone acetate: The required amount of hydrocortisone acetate was weighed and added to the main batch while mixing with homogenizer set at 4000-4500 RPM and equipped with a square shape mesh for ten minutes or until visibly uniformly dispersed. The temperature was maintained at 55±5° C. ($T_f$).

Filling process: Begin mixing the batch using a propeller type mixer (e.g. IKA) at 500-1500 RPM. The suspended hydrocortisone acetate must be kept from settling during the filling operation. Maintain batch temperature between 50-60° C. Set up a peristaltic pump (or similar) along with the tubing and adjust the settings so that it dispenses two grams of product in each cycle. The tubing was maintained at 50-60° C. with the help of a heat tape to avoid product congealing in the tube during filling into the suppositories. Dispense one cycle of product into each suppository form and allow to cool to room temperature. The cooling process may be accelerated by placing the filled forms into a cooling tunnel (or equivalent).

The relevant teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims of this provisional application or a later-filed non-provisional application claiming priority hereto.

What is claimed is:

1. A suppository having a weight of about 2 g and comprising about 90 mg hydrocortisone acetate, about 5 mg to about 20 mg colloidal silicon dioxide and an oleaginous base that includes triglycerides, wherein the suppository releases at least about 80% of the hydrocortisone acetate at about 180 minutes following exposure to dissolution media comprising a buffered 5% w/v sodium lauryl sulfate solution having a final pH in the range of about 6.8-7.0.

2. The suppository of claim 1, comprising about 14 mg colloidal silicon dioxide.

3. The suppository of claim 1, wherein the oleaginous base is a semi-synthetic glyceride base comprising saturated C8-C18 triglyceride fatty acids and lecithin.

4. The suppository of claim 1, wherein the oleaginous base comprises at least about 85% triglycerides, and further comprises diglycerides and monoglycerides.

5. The suppository of claim 1, further comprising about 0.01 mg to about 0.2 mg butylated hydroxytoluene (BHT).

6. The suppository of claim 1, wherein the suppository releases the hydrocortisone acetate upon exposure to rectal fluid.

7. The suppository of claim 1, wherein the suppository has a melting temperature in the range of about 37° C. to about 39° C.

8. The suppository of claim 1, wherein the suppository is stable under storage conditions at a temperature in the range of about 25° C. to about 40° C.

9. A formulation comprising about 0.5% to about 5% by weight hydrocortisone acetate, about 0.1% to about 5% by weight colloidal silicon dioxide and a semi-synthetic glyceride base comprising saturated C8-C18 triglyceride fatty acids and lecithin, wherein the formulation has a melting temperature in the range of about 37° C. to about 39° C.

10. The formulation of claim 9, comprising about 4.5% by weight hydrocortisone acetate and about 0.7% by weight colloidal silicon dioxide.

11. The formulation of claim 9, wherein the base comprises at least about 85% triglycerides, and further comprises diglycerides and monoglycerides.

12. The formulation of claim 9, wherein the formulation releases the hydrocortisone acetate upon exposure to rectal fluid.

* * * * *